US009089590B2

(12) United States Patent
Mohapatra et al.

(10) Patent No.: US 9,089,590 B2
(45) Date of Patent: Jul. 28, 2015

(54) POLYNUCLEOTIDES FOR REDUCING RESPIRATORY SYNCYTIAL VIRUS GENE EXPRESSION

(71) Applicant: UNIVERSITY OF SOUTH FLORIDA, Tampa, FL (US)

(72) Inventors: Shyam S. Mohapatra, Lutz, FL (US); Weidong Zhang, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 142 days.

(21) Appl. No.: 13/765,858

(22) Filed: Feb. 13, 2013

(65) Prior Publication Data

US 2013/0217751 A1 Aug. 22, 2013

Related U.S. Application Data

(63) Continuation of application No. 10/581,580, filed as application No. PCT/US2004/040727 on Dec. 6, 2004, now abandoned.

(60) Provisional application No. 60/481,738, filed on Dec. 4, 2003, provisional application No. 60/522,180, filed on Aug. 26, 2004.

(51) Int. Cl.

| | |
|---|---|
| ***C07H 21/04*** | (2006.01) |
| ***C12N 15/11*** | (2006.01) |
| ***A61K 31/713*** | (2006.01) |
| ***A61K 31/70*** | (2006.01) |
| ***C07H 21/02*** | (2006.01) |
| ***C12N 15/113*** | (2010.01) |

(52) U.S. Cl.

CPC ............... *A61K 31/713* (2013.01); *A61K 31/70* (2013.01); *C07H 21/02* (2013.01); *C07H 21/04* (2013.01); *C12N 15/1131* (2013.01); *C12N 2310/111* (2013.01); *C12N 2310/14* (2013.01)

(58) Field of Classification Search

None

See application file for complete search history.

(56) References Cited

U.S. PATENT DOCUMENTS

| | | | |
|---|---|---|---|
| 5,290,540 | A | 3/1994 | Prince et al. |
| 5,693,532 | A | 12/1997 | McSwiggen et al. |
| 5,831,069 | A | 11/1998 | Barik |
| 5,998,602 | A | 12/1999 | Torrence et al. |
| 6,136,597 | A | 10/2000 | Hope et al. |
| 6,391,318 | B1 | 5/2002 | Illum et al. |
| 6,489,306 | B2 | 12/2002 | Mohapatra et al. |
| 6,586,579 | B1 | 7/2003 | Huang |
| 6,852,528 | B2 | 2/2005 | Yu et al. |
| 6,900,299 | B1 | 5/2005 | Mohapatra et al. |
| 7,056,704 | B2 | 6/2006 | Tuschl et al. |
| 7,067,633 | B2 | 6/2006 | Kumar et al. |
| 7,118,888 | B2 | 10/2006 | Mohapatra et al. |
| 7,354,908 | B2 | 4/2008 | Mohapatra et al. |
| 7,425,618 | B2 | 9/2008 | Oliver et al. |
| 7,595,303 | B1 | 9/2009 | Mohapatra et al. |
| 7,655,772 | B2 | 2/2010 | Mohapatra |
| 2001/0006951 | A1 | 7/2001 | Mohapatra et al. |
| 2002/0173478 | A1 | 11/2002 | Gewirtz |
| 2003/0068333 | A1 | 4/2003 | Mohapatra et al. |
| 2003/0139363 | A1 | 7/2003 | Kay et al. |
| 2003/0143732 | A1 | 7/2003 | Fosnaugh et al. |
| 2003/0148519 | A1 | 8/2003 | Engelke et al. |
| 2003/0157691 | A1 | 8/2003 | Qin et al. |
| 2003/0166282 | A1 | 9/2003 | Brown et al. |
| 2003/0170891 | A1 | 9/2003 | McSwiggen |
| 2003/0175772 | A1 | 9/2003 | Wang |
| 2003/0175950 | A1 | 9/2003 | McSwiggen |
| 2003/0190635 | A1 | 10/2003 | McSwiggen |
| 2003/0198624 | A1 | 10/2003 | Mohapatra et al. |
| 2004/0002077 | A1 | 1/2004 | Taira et al. |
| 2004/0002458 | A1 | 1/2004 | Seilhamer et al. |
| 2004/0009152 | A1 | 1/2004 | Mohapatra et al. |
| 2004/0018176 | A1 | 1/2004 | Tolentino et al. |
| 2004/0019001 | A1 | 1/2004 | McSwiggen |
| 2004/0023390 | A1 | 2/2004 | Davidson et al. |
| 2004/0029275 | A1 | 2/2004 | Brown et al. |
| 2004/0175384 | A1 | 9/2004 | Mohapatra et al. |
| 2004/0242518 | A1 | 12/2004 | Chen et al. |
| 2004/0259247 | A1 | 12/2004 | Tuschl et al. |
| 2005/0096291 | A1 | 5/2005 | Iversen et al. |
| 2005/0106598 | A1 | 5/2005 | Manoharan et al. |
| 2005/0158327 | A1 | 7/2005 | Mohapatra et al. |
| 2005/0159385 | A1 | 7/2005 | Mohapatra |
| 2005/0266093 | A1 | 12/2005 | Mohapatra |
| 2005/0272650 | A1 | 12/2005 | Mohapatra |
| 2006/0239971 | A1 | 10/2006 | Mohapatra et al. |

(Continued)

FOREIGN PATENT DOCUMENTS

| | | | |
|---|---|---|---|
| WO | WO 03/028759 | A1 | 4/2003 |
| WO | WO 03/070918 | A2 | 8/2003 |

(Continued)

OTHER PUBLICATIONS

Song et al (Nature Medicine 9(3): 347-351, Feb. 10, 2003).*

McCaffrey AP et al., "RNA interference in adult mice" *Nature*, 2002, 418:38-39.

Houng HHS et al., "Development of a flurogenic RT-PCR system for quantititative identification of dengue virus serotypes 1-4 using conserved and serotype-specific 3' noncoding sequences" *Journal of Virological Methods*, 2001, 95:19-32.

U.S. Appl. No. 10/655,873, filed Sep. 5, 2003, Mohapatra et al.

Abbas-Terki, T. et al. "Lentiviral-Mediated RNA Interference" Human Gene Therapy, 2002, 13:2197-2201.

(Continued)

*Primary Examiner* — Richard Schnizer

(74) *Attorney, Agent, or Firm* — Saliwanchik, Lloyd & Eisenschenk

(57) ABSTRACT

This invention pertains to polynucleotides, such as small interfering RNA (siRNA), useful for reducing the expression of respiratory syncytial virus (RSV) genes within a subject; and methods for treating a patient suffering from, or at risk of developing, an RSV infection by administering such polynucleotides to the subject.

6 Claims, 15 Drawing Sheets
(3 of 15 Drawing Sheet(s) Filed in Color)

(56) References Cited

U.S. PATENT DOCUMENTS

2006/0276382 A1 12/2006 Mohapatra
2007/0009951 A1 1/2007 Mohapatra et al.
2007/0031844 A1 2/2007 Khvorova et al.
2007/0116767 A1 5/2007 Mohapatra et al.
2007/0265204 A1 11/2007 Mohapatra et al.
2008/0023325 A1 1/2008 Mohapatra et al.
2008/0070858 A1 3/2008 Mohapatra
2008/0075731 A1 3/2008 Mohapatra et al.
2008/0100279 A1 5/2008 Mohapatra et al.
2008/0249057 A1 10/2008 Mohapatra et al.
2009/0280143 A1 11/2009 Mohapatra et al.

FOREIGN PATENT DOCUMENTS

WO WO 03/092618 11/2003
WO WO 2004/074314 A2 9/2004
WO WO 2005/094420 10/2005
WO WO 2005/105136 11/2005
WO WO/2007/127480 11/2007
WO WO 2007/127487 11/2007

OTHER PUBLICATIONS

Adelman, Z.N. et al. "RNA silencing of dengue virus type 2 replication in transformed C6/36 mosquito cells transcribing an inverted-repeat RNA derived from the virus genome" *J. Virology*, 2002, 76:12925-12933.

Adelman, Z.N. et al. "*Sindbis virus*-induced silencing of dengue viruses in mosquitoes" *Insect Mol Biol.*, 2001, 10:265-273.

Agrawal, N. et al. "RNA Interference: Biology, Mechanism, and Applications" *Microbiology and Molecular Biology Reviews*, 2003, 67(4):657-685.

An, J. et al. "Development of a Novel Mouse Model for Dengue Virus Infection" *Virology*, Oct. 1999, 263:70-77.

Anderson, W.F. "Human Gene Therapy" Nature, 1998, pp. 25-30, vol. 392.

Banchereau, J. and Steinman, R.M. "Dendritic cells and the control of immunity" *Nature*, 1998, 392:245-252.

Barratt-Boyes, S. et al. "Maturation and Trafficking of Monocyte-Derived Dendritic Cells in Monkeys: Implications for Dendritic Cell-Based Vaccines" *The Journal of Immunology*, 2000, 164:2487-2495.

Behera, A.K. et al. "2'-5' Oligoadenylate Synthetase Plays a Critical Role in Interferon-Γ Inhibition of Respiratory Syncytial Virus Infection of Human Epithelial Cells" J. Biol. Chem, 2002, pp. 25601-25608, vol. 277, No. 28.

Behera, A.K. et al. "Adenovirus Mediated Interferon Γ Gene Therapy for Allergic Asthma: Involvement of Interleukin 12 and STAT4 Signaling" Hum. Gene Ther., 2002, pp. 1697-1709, vol. 13.

Bitko, V. et al. "Phenotypic silcencing of cytoplasmic genes using sequence-specific double-stranded short interfering RNA and its application in the reverse genetics of wild type negative-strand RNA viruses" *BMC Microbiology*, 2001, 1:34.

Blair, C.D. et al. "Molecular strategies for interrupting arthropod-borne virus transmission by mosquitoes" *Clin Microbiol Rev*, 2000, 13:651-661.

Bossert, B. et al. "Nonstructural Proteins NS1 and NS2 of Bovine Respiratory Syncytial Virus Block Activation of Interferon Regulatory Factor 3" J. Virol., 2003, pp. 8661-8668, vol. 77, No. 16.

Bossert, B. et al. "Respiratory Syncytial Virus (RSV) Nonstructural (NS) Protein as Host Range Determinants: A Chimeric Bovine RSV With NS Genes From Human RSV Is Attenuated in Interferon-Competent Bovine Cells" J. Virol., 2002, pp. 4287-4293, vol. 76, No. 9.

Bueler, H. "Adeno-associated viral vectors for gene transfer and gene therapy" *Biol Chem*, 1999, 380:613-622, abstract.

Caplen, N. "RNAI as a Gene Therapy Approach" Expert Opin. Biol. Ther., 2003, pp. 575-586, vol. 3, No. 4.

Caplen, N. et al. "Specific inhibition of gene expression by small double-stranded RNAs in invertebrate and vertebrate systems" *Proc. Natl. Acad. Sci. USA*, 2001, 98:9742-9747.

Caplen, N.J. et al. "Inhibition of viral gene expression and replication in mosquito cells by dsRNA-triggered RNA interference" *Mol Ther*, 2002, 6:243-251.

Chhabra, A. et al. "Silencing of Endogenous IL-10 in Human Dendritic Cells Leads to the Generation of an Improved CTL Response Against Human Melanoma Associated Antigenic Epitope, MART-1" *Clin Immunol.*, Mar. 2008, 126(3):251-259.

Coburn, G.A. et al. "siRNAs: a new wave of RNA-based therapeutics" *Journal of Antimicrobial Chemotherapy*, 2003, 51:753-756.

Condon, C. et al. "DNA-based immunization by in vivo transfection of dendritic cells" *Nature Medicine*, Oct. 1996, 2(10):1122-1128.

Deplamche, M. et al. "In Vivo Evidence for Quasispecies Distributions in the Bovine Respiratory Syncytial Virus Genome" 2007, pp. 1260-1265, vol. 88, NCBI Accession No. NC_001989.

Dorn, G. et al. "SIRNA Relieves Chronic Neuropathic Pain" Nucleic Acids Res., 2004, pp. E49, vol. 32.

Elbashir, S.M. et al. "Duplexes of 21-nucleotide RNAs mediate RNA interference in cultured mammalian cells" *Nature*, 2001, 411:494-498.

Fire, A. "RNA-triggered gene silencing" *Trends Genet*, 1999, 15:358-363.

Hallak, L.K. et al. "Iduronic Acid-Containing Glycosaminoglycans on Target Cells Are Required for Efficient Respiratory Syncytial Virus Infection" Virology, 2000, pp. 264-275, vol. 271.

Hammond, S.M. et al. "Argonaute2, a link between genetic and biochemical analyses of RNAi" *Science*, 2001, 293:1146-1150.

Heale, B.S.E. et al. "siRNA target site secondary structure predictions using local stable substructures" *Nucleic Acids Research*, 2005, 33(3):e30, pp. 1-10.

Hellermann, G. et al. "Genetic Therapy: On the Brink of a New Future" Genetic Vaccines and Ther., 2003, pp. 1-3, vol. 1.

Hill, J.A. et al. "Immune Modulation by Silencing IL-12 Production in Dendritic Cells Using Small Interfering RNA" *The Journal of Immunology*, 2003, 171:691-696.

Ho, L.J. et al. "Infection of human dendritic cells by dengue virus causes cell maturation and cytokine production" *J Immunol*, 2001, 166:1499-1506.

Hu, W-Y. et al. "Inhibition of Retroviral Pathogenesis by RNA Interference" *Current Biology*, Aug. 6, 2002, 12:1301-1311.

Hutvágner, G. et al. "A cellular function for the RNA-interference enzyme dicer in the maturation of the let-7 small temporal RNA" *Science*, 2001, 293:834-838.

Ilves, H. et al. "Retroviral Vectors Designed for Targeted Expression of RNA Polymerase III-Driven Transcripts: A Comparative Study" Gene, 1996, 171:203-208.

Jairath, S. et al. "Inhibition of Respiratory Syncytial Virus Replication by Antisense Oligodeoxyribonucleotides" Antiviral Res., 1997, 33:201-213.

Jessie, K. et al. "Localization of Dengue Virus in Naturally Infected Human Tissues, by Immunohistochemistry and In Situ Hybridization" The Journal of Infectious Diseases, 2004, pp. 1411-1418, vol. 189.

Jin, H. et al. "Recombinant Respiratory Syncytial Viruses With Deletions in the NS1, NS2, SH, and M2-2 Genes Are Attenuated In Vitro and In Vivo" Virology, 2000, pp. 210-218, vol. 273.

Kay, M.A. et al. "Viral Vectors for Gene Therapy: The Art of Turning Infectious Agents Into Vehicles of Therapeutics" Nature Med, 2001, 7:33-40.

Kretschmer-Kazemi, R. et al. "The activity of siRNA in mammalian cells is related to structural target accessibility: a comparison with antisense oligonucleotides" *Nucleic Acids Research*, 2003, 31(15):4417-4424.

Kumar, M. et al. "Chitosan IFN-Γ-PDNA Nanoparticles (CIN) Therapy for Allergic Asthma" Genetic Vaccines and Ther., 2003, pp. 3, vol. 1.

Kumar, M. et al. "Intranasal Gene Transfer by Chitosan-DNA Nanospheres Protects BALB/C Mice Against Acute Respiratory Syncytial Virus Infection" Human Gene Ther., 2002, pp. 1415-1425, vol. 13.

Kumar, M. et al. "Intranasal IFN-Γ Gene Transfer Protects BALB/C Mice Against Respiratory Syncytial Virus Infection" Vaccine, 1999, pp. 558-567, vol. 18.

(56) References Cited

OTHER PUBLICATIONS

Larregina, A.T. et al. "Direct transfection and activation of human cutaneous dendritic cells" *Gene Therapy*, 2001, 8:608-617.
Lazar, I. et al. "Human Metapneumovirus and Severity of Respiratory Syncytial Virus Disease" 2004, pp. 1318-1320, vol. 10, No. 7, NCBI Accession No. M74568.
Leaman, D.W. et al. "Targeted Therapy of Respiratory Syncytial Virus in African Green Monkeys by Intranasally Administered 2-5A Antisense" Virology, 2002, pp. 70-77, vol. 292.
Li, M. et al. "Immune Modulation and Tolerance Induction by ReIB-Silenced Dendritic Cells through RNA Interference" *The Journal of Immunology*, 2007, 178:5480-5487.
Libraty, D.H. et al. "Human Dendritic Cells Are Activated by Dengue Virus Infection: Enhancement by Gamma Interferon and Implications for Disease Pathogenesis" J Virol, 2001, 75:3501-3508.
Lieberman, J. et al. "Interfering with disease: opportunities and roadblocks to harnessing RNA interference" *TRENDS in Molecular Medicine*, Sep. 2003, 9(9):397-403.
Liu, F. et al. "Hydrodynamics-based transfection in animals by systemic administration of plasmid DNA" *Gene Therapy*, 1999, 6:1258-1266.
Ludewig, B. et al. "Protective Antiviral Cytotoxic T Cell Memory Is Most Efficiently Maintained by Restimulation Via Dendritic Cells" J Immunol, 1999, 163:1839-1844.
Marovich, M. et al. "Human Dendritic Cells as Targets of Dengue Virus Infection" J Investig Dermatol Symp Proc., 2001, 6:219-224.
Matsuse, H. et al. "Recurrent Respiratory Syncytial Virus Infections in Allergen-Sensitized Mice Lead to Persistent Airway Inflammation and Hyperresponsiveness" J. Immunol., 2000, pp. 6583-6592, vol. 164.
Men, R. et al. "Dengue Type 4 Virus Mutants Containing Deletions in the 3' Noncoding Region of the RNA Genome: Analysis of Growth Restriction in Cell Culture and Altered Viremia Pattern and Immunogenicity in Rhesus Monkeys" J Virol. 1996, 70:3930-3937.
Milhavet, O. et al. "RNA Interference in Biology and Medicine" *Pharmacological Reviews*, 2003, 55(4):629-648.
Miyagishi M et al., "Comparison of the Suppressive Effects Antisense Oligonucleotides and siRNAs Directed Against the Same Targets in Mammalian Cells," *Antisense and Nucleic Acid Drug Development*, Feb. 2003, 13(1):1-7.
Mohapatra, S.S. "Mucosal Gene Expression Vaccine: A Novel Vaccine Strategy for Respiratory Syncytial Virus" Pediatr. Infect. Dis. J., 2003, pp. S100-S104, vol. 22, No. 2.
Murphy, B.R. et al. "Live-Attenuated Virus Vaccines for Respiratory Syncytial and Parainfluenza Viruses: Applications of Reverse Genetics" J. Clin. Invest., 2002, pp. 21-27, vol. 110, No. 1.
Nair, M.P.N. et al. "RNAi-directed Inhibition of DC-SIGN by Dendritic Cells: Prospects for HIV-1 Therapy" *The AAPS Journal*, 2005, 7(3):E572-E578.
Nawtaisong, P. et al. "Effective suppression of Dengue fever virus in mosquito cell cultures using retroviral transduction of hammerhead ribozymes targeting the viral genome" *Virology Journal*, 2009, 6:73, pp. 1-17.
Paddison PJ et al. "Short hairpin RNAs (shRNAs) induce sequence-specific silencing in mammalian cells" *Genes & Development*, 2002, 16:948-958.
Paddison, P.J. et al. "Stable Suppression of Gene Expression by RNAI in Mammalian Cells" PNAS, 2002, pp. 1443-1448, vol. 99, No. 3.
Palmowski, M.J. et al. "Intravenous Injection of a Lentiviral Vector Encoding NY-ESO-1 Induces an Effective CTL Response" *Journal of Immunology*, 2004, 172:1582-1587.
Pan, W. et al. "Isolation of Virus-Neutralizing RNAS From a Large Pool of Random Sequences" Proc. Natl. Acad. Sci. USA, 1995, 92:11509-11513.
Paul, C.P. et al. "Effective Expression of Small Interfering RNA in Human Cells" Nature Biotech., 2002, 20:505-508.
Ponnazhagan, S. et al. "Adeno-Associated Virus Type 2-Mediated Transduction of Human Monocyte-Derived Dendritic Cells: Implications for Ex Vivo Immunotherapy" J Virol, 2001, 75:9493-9501.
Porgador, A. et al. "Predominant Role for Directly Transfected Dendritic Cells in Antigen Presentation to CD8$^+$T Cells after Gene Gun Immunization" *The Journal of Experimental Medicine*, Sep. 21, 1998, 188(6):1075-1082.
Proutski, V. et al. "Secondary Structure of the 3' Untranslated Region of Flaviviruses: Similarities and Differences" Nucleic Acids Res, 1997, 25:1194-1202.
Provost, P. et al. "Ribonuclease Activity and RNA Binding of Recombinant Human Dicer" EMBO J, 2002, 21:5864.
Qian, H. et al. "Silencing CD40 in Dendritic Cells by siRNA" *12$^{th}$ International Congress of Immunology and 4$^{th}$ Annual Conference of FOCIS, Montreal, Canada*, Jul. 18-23, 2004, 2004, pp. 339-348.
Rauscher, S. et al. "Secondary Structure of the 3'-Noncoding Region of Flavivirus Genomes: Comparative Analysis of Base Pairing Probabilities" RNA, 1997, 3:779-791.
Raviprakash, K. et al. "Inhibition of Dengue Virus by Novel, Modified Antisense Oligonucleotides" Journal of Virology, 1995, pp. 69-74, vol. 69, No. 1.
Reich, S.J. et al. "Small Interfering RNA (SIRNA) Targeting VEGF Effectively Inhibits Ocular Neovascularization in a Mouse Model" Mol. Vis., 2003, pp. 210-216, vol. 9.
Romano, G. et al. "Latest Developments in Gene Transfer Technology: Achievements, Perspectives, and Controversies Over Therapeutic Applications" Stem Cells, 2000, pp. 19-39, vol. 18.
Rosenberg, L. E. et al. "Gene Therapist, Heal Thyself" Science, 2000, pp. 1751, vol. 287.
Roy, K. et al. "Oral Gene Delivery With Chitosan-DNA Nanoparticles Generates Immunologic Protection in a Murine Model of Peanut Allergy" Nat Med, 1999, 5:387-391.
Schlender, J. et al. "Bovine Respiratory Syncytial Virus Nonstructural Proteins NS1 and NS2 Cooperatively Antagonize Alpha/Beta Interferon-Induced Antiviral Response" J. Virol., 2000, pp. 8234-8242, vol. 74, No. 18.
Shao, Y. et al. "Effect of target secondary structure on RNAi efficiency" *RNA*, 2007, 13:1631-1640.
Somia, N. et al. "Gene Therapy: Trials and Tribulations" Nature Reviews, 2000, pp. 91-99, vol. 1.
Song, E. et al. "Antigen presentation in retroviral vector-mediated gene transfer in vivo" *Proc. Natl. Acad. Sci, USA*, Mar. 1997, 94:1943-1948.
Soutschek, J. et al. "Therapeutic Silencing of an Endogenous Gene by Systemic Administration of Modified SIRNAS" Nature, 2004, pp. 173-178, vol. 432.
Spann, K.M. et al., "Suppression of the Induction of Alpha, Beta, and Gamma Interferons by the NS1 and NS2 Proteins of Human Respiratory Syncytial Virus in Human Epithelial Cells and Macrophages" J. Virol., 2004, pp. 4363-4369, vol. 78, No. 8.
Srivastava, A. "Obstacles to Human Hematopoietic Stem Cell Transduction by Recombinant Adeno-Associated Virus 2 Vectors" J Cell Biochem Suppl, 2002, 38:39-45.
Stämpfli, M.R. et al. "GM-CSF Transgene Expression in the Airway Allows Aerosolized Ovalbumin to Induce Allergic Sensitization in Mice" J Clin Invest, 1998, 102:1704-1714.
Stark, G.R. et al. "How Cells Respond to Interferons" Annu Rev Biochem, 1998, 67:227-264.
Stein, C.A. "The Experimental Use of Antisense Oligonucleotides: A Guide for the Perplexed" J. Clin. Invest., 2001, 108:641-644.
Subramanya, S. et al. "Targeted Delivery of Small Interfering RNA to Human Dendritic Cells to Suppress Dengue Virus Infection and Associated Proinflammatory Cytokine Production" *Journal of Virology*, Mar. 2010, 84(5):2490-2501.
Teng, M.N. et al. "Altered Growth Characteristics of Recombinant Respiratory Syncytial Viruses Which Do Not Produce NS2 Protein" J. Virol., 1999, pp. 466-473, vol. 73.
Teng, M.N. et al. "Recombinant Respiratory Syncytial Virus That Does Not Express the NS1 or M2-2 Protein Is Highly Attenuated and Immunogenic in Chimpanzees" J. Virol., 2000, pp. 9317-9321, vol. 74, No. 19.
Tolentino, M.J. et al. "Intravitreal Injection of Vascular Endothelial Growth Factor Small Interfering RNA Inhibits Growth and Leakage in a Nonhuman Primate, Laser-Induced Model of Choroidal Neovascularization" *Retina*, 2004, 24:132-138.

(56) References Cited

OTHER PUBLICATIONS

Tuschl, T. "Expanding Small RNA Interference" Nature Biotechnol., 2002, 20:446-448.

Vaughn, D.W. et al. "Dengue in the Early Febrile Phase: Viremia and Antibody Responses" J Infect Dis, 1997, 176:322-330.

Verma, I.M. et al. "Gene Therapy—Promises, Problems and Prospects" Nature, 1997, pp. 239-242, vol. 389.

Walter, D.M. et al. "IL-18 Gene Transfer by Adenovirus Prevents the Development of and Reverses Established Allergen-Induced Airway Hyperreactivity" J Immunol, 2001, 166:6392-6398.

Westerhout, E.M. et al. "A systematic analysis of the effect of target RNA structure on RNA interference" *Nucleic Acids Research*, 2007, 35(13):4322-4330.

Wu, S.J. et al. "Human Skin Langerhans Cells Are Targets of Dengue Virus Infection" Nature Med, 2000, 6:816-820.

Yoshinari, K. et al. "Effects on RNAi of the tight structure, sequence and position of the targeted region" *Nucleic Acids Research*, 2004, 32(2):691-699.

Yu, J. et al. "RNA Interference by Expression of Short-Interfering RNAS and Hairpin RNAS in Mammalian Cells" PNAS, 2002, pp. 6047-6052, vol. 99, No. 9.

Zaiss, A-K. et al. "Differential Activation of Innate Immune Responses by Adenovirus and Adeno-Associated Virus Vectors" J Virol, 2002, 76:4580-4590.

Zhang, W. et al. "Attenuation of Dengue Virus Infection by Adeno-Associated Virus-Mediated SIRNA Delivery" Genetic Vaccines Ther., 2004, pp. 8, vol. 2.

Zhang, X. et al. "Small Interfering RNA Targeting HEME Oxygenase-1 Enhances Ischemia-Reperfusion-Induced Lung Apoptosis" J. Biol. Chem., 2004, pp. 10677-10684, vol. 279, No. 11.

Zimmerman, T.S. et al. "RNAi-mediated gene silencing in non-human primates" *Nature*, May 2006, 441:111-114.

* cited by examiner

Figures 2A, 2B:
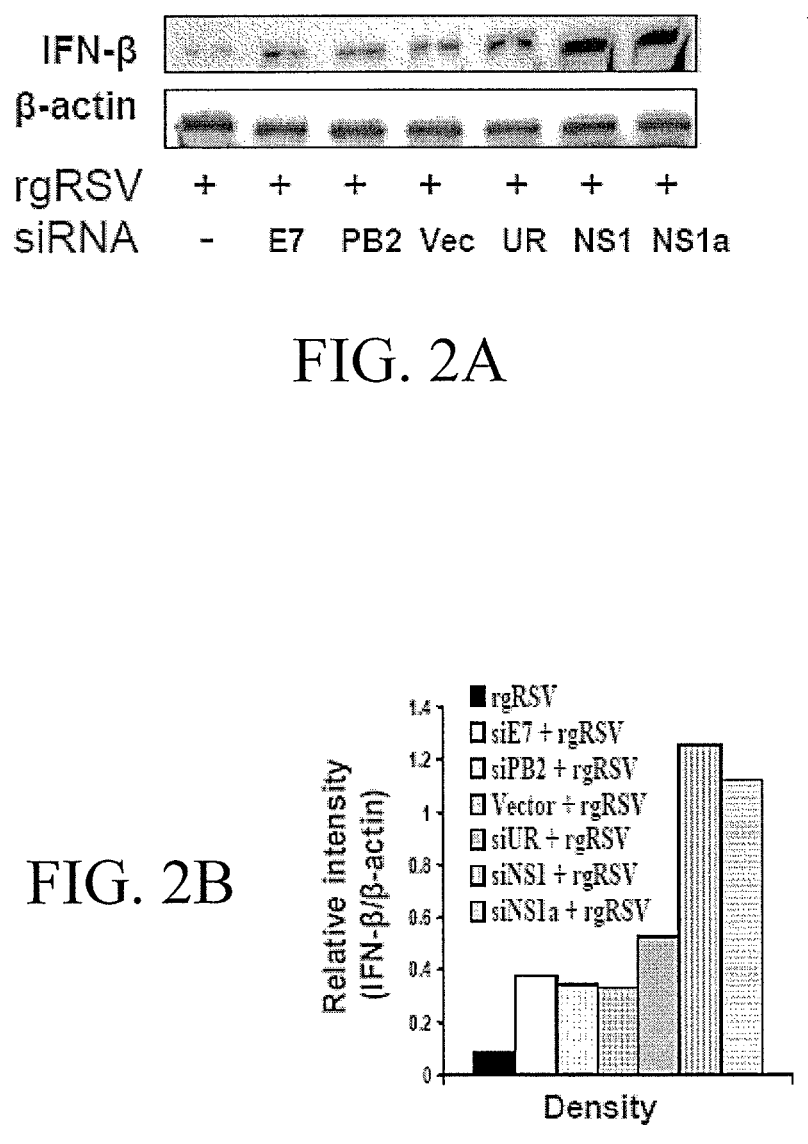

IFN-β
β-actin
rgRSV + + + + + + +
siRNA - E7 PB2 Vec UR NS1 NS1a

■ rgRSV
□ siE7 + rgRSV
□ siPB2 + rgRSV
□ Vector + rgRSV
□ siUR + rgRSV
□ siNS1 + rgRSV
□ siNS1a + rgRSV Relative intensity (IFN-β/β-actin)

1.4
1.2
1
0.8
0.6
0.4
0.2
0

Density

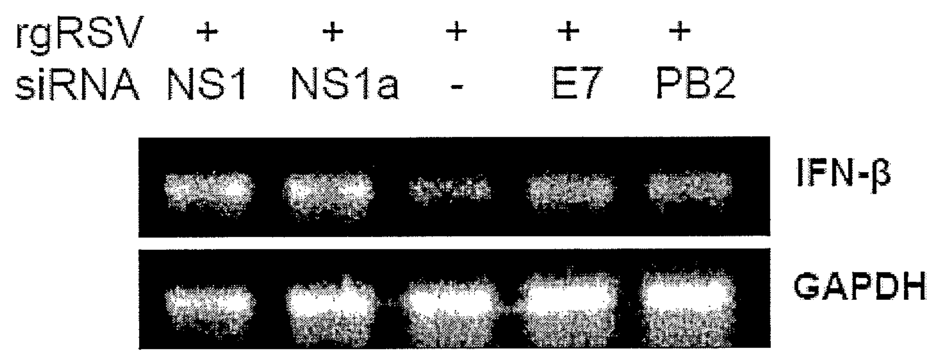
FIG. 4H
FIG. 4I
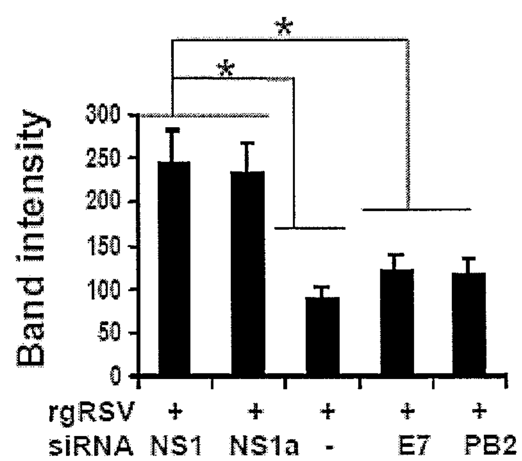

| | | | | | | | | | | | | | | | | | | | |
|---|---|---|---|---|---|---|---|---|---|---|---|---|---|---|---|---|---|---|---|
| pCIS-CK | + | + | + | | | | | | | | | | | | | | | | |
| pISRE | | | | + | + | + | + | + | + | + | + | + | + | + | + | + | + | + | + |
| pVAX | | | | | | | | | | | + | | | | | | | | |
| pVAX-F | | | | | | | | | | | | | + | + | + | | | | |
| pVAX-NS1 | + | | | | | | | | | | | + | | | | + | + | + | + |
| siNS1 | | + | | | | | + | | | | | | | + | | + | | | |
| siNS1a | | | | | | | | + | | | | | | | | | + | | |
| siE7 | | | + | | | | | | + | | | | | | + | | | + | |
| siPB2 | | | | | | | | | | + | | | | | | | | | + |
| Vector | | | | | | + | | | | | | | | | | | | | |
| UR-siRNA | | | | | + | | | | | | | | | | | | | | |
| Poly(I)(C) | | | | | | | | | | | | + | + | + | + | + | + | + | + |

FIG. 6B

POLYNUCLEOTIDES FOR REDUCING RESPIRATORY SYNCYTIAL VIRUS GENE EXPRESSION

CROSS-REFERENCE TO RELATED APPLICATIONS

This application is a continuation of U.S. application Ser. No. 10/581,580, filed Mar. 29, 2007; which is the National Stage of International Application Number PCT/US2004/040727, filed Dec. 6, 2004, which claims benefit of U.S. Provisional Application Ser. No. 60/481,738, filed Dec. 4, 2003; and U.S. Provisional Application Ser. No. 60/522,180, filed Aug. 26, 2004, each of which is hereby incorporated by reference herein in its entirety, including any figures, tables, nucleic acid sequences, amino acid sequences, and drawings.

BACKGROUND OF THE INVENTION

Respiratory syncytial virus (RSV) a major viral respiratory pathogen and is the leading cause of lower respiratory tract infection in infant, young children and the elderly with immunocompromise (Collins, P. L. et at Respiratory syncytial virus. In: D. M. Knipe, P. M. Howley and D. E. Griffin, Editors, 4th ed., Fields Virology Vol. 1, Lippincott-Raven, Philadelphia, 2001, pp. 1443-1485), and is also a risk factor for the development of asthma (Behera, A. K. et al. *J Biol Chem,* 2002, 277:25601-25608). RSV produces an annual epidemic of respiratory illness, causing bronchitis and otitis media in infants and young children (Sigurs, N. et al. *Am J Respir Crit Care Med.,* 2000, 161:1501-1507; Sigurs, N. et al. *Pediatrics,* 1995, 95:500-505) and pneumonia in adults and the elderly (Shay, D. K. et al. *JAMA,* 1999, 282:1440-1446; Hall, C. B. et al. *Clin Infect Dis.,* 2001, 33:792-796). Immunodeficiency, cardiac arrhythmia, and congenital heart disease are risk factors for more severe diseases with RSV infection (Sly, P. D. et al. *Pediatr. Pulmonol.,* 1989, 7:153-158; Brandenburg, A. H. et al. *Vaccine,* 2001, 19:2769-2782; Coffin, S. E. and Offit, P. A., *Adv. Pediatr. Infect. Dis.,* 1997, 13:333-348).

Previous RSV infection does not prevent subsequent infections, even in sequential years (Bartz, H. et al. *Immunology,* 2003, 109:49-57). In the Unites States alone, the severe viral bronchiolitis and pneumonia results in approximately 100,000 hospitalizations and 4500 deaths in infants and young children each year (Carbonell-Estrany, X. and Quero, J. *Pediatr Infect Dis J,* 2001, 20:874-879; Hall, C. B. *Clin Infect Dis.,* 2000, 31:590-596). During the period of 1991-1998, RSV was associated annually with over 17,000 deaths (Thompson. W. W. et al., *JAMA,* 2003, 289:179-186). To date, there are no specific antiviral treatments available. Although many different approaches are being taken to develop prophylactic vaccines, none have been licensed for public health use to prevent diseases associated with RSV infection.

RSV is the prototypic member of the *Pneumovirus* genus of the Paramyxoviridae family and is an enveloped nonsegmented negative-stranded RNA virus. The RSV genome of approximately 15,200 nucleotides is transcribed into 10 transcripts, which encodes 11 distinct viral proteins in the order: NS1, NS2, N, P, M, SH, G, F, M2-1, M2-2, and L. Three RSV envelope glycoproteins involves the fusion F protein, the attachment glycoprotein G and the small hydrophobic SH protein. An unglycosylated matrix M protein is present as an inner virion protein. And the nucleocapsid is composed of the major nucleocapsid protein N, P phosphoprotein, large L polymerase subunit and M2-1 protein. Two nonstructural proteins NS1 and NS2 are expressed from separate mRNAs encoded by the first and second genes, respectively, that follow the 44-nt leader region (Collins, P. L. et al Respiratory syncytial virus. In: D. M. Knipe, P. M. Howley and D. E. Griffin, Editors, 4th ed., Fields Virology Vol. 1, Lippincott-Raven, Philadelphia, 2001, pp. 1443-1485; Collins, P. L. and Wertz, G. W. *Virology,* 1985, 143:442-451). As their promoter-proximal location, these two mRNAs are the most abundant of the RSV transcripts in a linear start-stop-restart mode (Collins, P. L. et al Respiratory syncytial virus. In: D. M. Knipe, P. M. Howley and D. E. Griffin, Editors, 4th ed., Fields Virology Vol. 1, Lippincott-Raven, Philadelphia, 2001, pp. 1443-1485). Deletion of either NS gene severely attenuates RSV infection in vivo and in vitro, indicating that NS proteins play an important role in viral replication cycle (Jin, H. et al. *Virology,* 2000, 273:210-208; Teng, M. N. and Collins, P. L. *J Virol,* 1999, 73:466-473; Teng, M. N. et al. *J Virol,* 2000, 74:9317-9321; Murphy, B. R. and Collins, P. L. *J Clin Invest.,* 2002, 110:21-27).

Clinical studies have shown that RSV infection in infants is associated with a predominantly Th2-like response (Roman, M. et al. *Am J Respir Crit Care Med.,* 1997, 156:190-195). Hence, RSV is considered a predisposing factor for the development of allergic diseases and asthma (Matsuse, H. et al. *J Immunol.,* 2000, 164:6583-6592; Behera, A. K. et al., *Hum. Gene Ther.,* 2002, 13:1697-1709).

Interferons (IFNs) attenuate RSV replication and also have therapeutic value against allergic diseases, including asthma (Kumar, M. et al. *Vaccine,* 1999, 18:558-567; Kumar, M. et al. *Human Gene Ther.,* 2002, 13:1415-1425; Kumar, M. et al. *Genetic Vaccines and Ther.,* 2003, 1:3-12). In addition, in vivo intranasal gene delivery approaches have been developed using nanoparticles composed of chitosan, a natural, biocompatible, and biodegradable polymer (Kumar, M. et al. *Human Gene Ther.,* 2002, 13:1415-1425; Kumar, M. et al. *Genetic Vaccines and Ther.,* 2003, 1:3-12; Mohapatra, S. S. *Pediatr Infect Dis J.,* 2003, 22:S100-S103; Hellerman, G. and Mohapatra, S. S. *Genetic Vaccines and Ther.,* 2003, 1:1-3). Since bovine and human RSV NS1 appear to antagonize the Type-I interferon-mediated antiviral response (Bossert, B. and Conzelmann, K. K. *J. Virol.,* 2002, 76:4287-4293; Bossert, B. et al. *J. Virol.,* 2003, 77:8661-8668; Schlender, J. et al. *J. Virol.,* 2000, 74:8234-8242; Spann, K. M. et al. *J. Virol.,* 2004, 78:4363-4369), it was reasoned that blocking NS gene expression might attenuate RSV replication and provide an effective antiviral and immune enhancement therapy.

A naturally occurring gene-silencing mechanism triggered by double-stranded RNA (dsRNA), designated as small interfering RNA (siRNA), has emerged as a very important tool to suppress or knock down gene expression in many systems. RNA interference is triggered by dsRNA that is cleaved by an RNAse-III-like enzyme, Dicer, into 21-25 nucleotide fragments with characteristic 5' and 3' termini (Provost, P. D. et al. *Embo J,* 2002, 21:5864). These siRNAs act as guides for a multi-protein complex, including a PAZ/PIWI domain containing the protein Argonaute2, that cleaves the target mRNA (Hammond, S. M. et al. *Science,* 2001, 293:1146-1150). These gene-silencing mechanisms are highly specific and potent and can potentially induce inhibition of gene expression throughout an organism. The short interference RNA (siRNA) approach has proven effective in silencing a number of genes of different viruses (Fire, A. *Trends Genet.,* 1999, 15:358-363).

RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., *Nature* 391:806-11 (1998); Sharp, *Genes Dev.* 13:139-41 (1999); Elbashir et al. *Nature* 411:494-98 (2001); Harborth et al., *J. Cell Sci.* 114:4557-65 (2001)). RNAi is mediated by double-stranded polynucleotides, such as double-stranded RNA (dsRNA), having sequences that correspond to exonic sequences encoding portions of the polypeptides for which expression is compromised. RNAi reportedly is not effected by double-stranded RNA polynucleotides that share sequence identity with intronic or promoter sequences (Elbashir et al., 2001). RNAi pathways have been best characterized in *Drosophila* and *Caenorhabditis elegans*, but "small interfering RNA" (siRNA) polynucleotides that interfere with expression of specific polynucleotides in higher eukaryotes such as mammals (including humans) have also been considered (e.g., Tuschl, 2001 *Chembiochem.* 2:239-245; Sharp, 2001 *Genes Dev.* 15:485; Bernstein et al., 2001 *RNA* 7:1509; Zamore, 2002 *Science* 296:1265; Plasterk, 2002 *Science* 296:1263; Zamore 2001 *Nat. Struct. Biol.* 8:746; Matzke et al., 2001 *Science* 293:1080; Scadden et al., 2001 *EMBO Rep.* 2:1107).

According to a current non-limiting model, the RNAi pathway is initiated by ATP-dependent, cleavage of long dsRNA into double-stranded fragments of about 18-27 (e.g., 19, 20, 21, 22, 23, 24, 25, 26, etc.) nucleotide base pairs in length, called small interfering RNAs (siRNAs) (see review by Hutvagner et al., *Curr. Opin. Gen. Dev.* 12:225-32 (2002); Elbashir et al., 2001; Nyknen et al., *Cell* 107:309-21 (2001); Zamore et al., *Cell* 101:25-33 (2000)). In *Drosophila*, an enzyme known as "Dicer" cleaves the longer double-stranded RNA into siRNAs; Dicer belongs to the RNase III family of dsRNA-specific endonucleases (WO 01/68836; Bernstein et al., *Nature* 409:363-66 (2001)). Further, according to this non-limiting model, the siRNA duplexes are incorporated into a protein complex, followed by ATP-dependent unwinding of the siRNA, which then generates an active RNA-induced silencing complex (RISC) (WO 01/68836). The complex recognizes and cleaves a target RNA that is complementary to the guide strand of the siRNA, thus interfering with expression of a specific protein (Hutvagner et al., supra).

In *C. elegans* and *Drosophila*, RNAi may be mediated by long double-stranded RNA polynucleotides (WO 99/32619; WO 01/75164; Fire et al., 1998; Clemens et al., *Proc. Natl. Acad. Sci.* USA 97:6499-6503 (2000); Kisielow et al., *Biochem. J.* 363:1-5 (2002); see also WO 01/92513 (RNAi-mediated silencing in yeast)). In mammalian cells, however, transfection with long dsRNA polynucleotides (i.e., greater than 30 base pairs) leads to activation of a non-specific sequence response that globally blocks the initiation of protein synthesis and causes mRNA degradation (Bass, *Nature* 411:428-29 (2001)). Transfection of human and other mammalian cells with double-stranded RNAs of about 18-27 nucleotide base pairs in length interferes in a sequence-specific manner with expression of particular polypeptides encoded by messenger RNAs (mRNA) containing corresponding nucleotide sequences (WO 01/75164; Elbashir et al., 2001; Elbashir et al., *Genes Dev.* 15:188-200 (2001)); Harborth et al., *J. Cell Sci.* 114:4557-65 (2001); Carthew et al., *Curr. Opin. Cell Biol.* 13:244-48 (2001); Mailand et al., *Nature Cell Biol.* Advance Online Publication (Mar. 18, 2002); Mailand et al. 2002 *Nature Cell Biol.* 4:317).

siRNA polynucleotides may offer certain advantages over other polynucleotides known to the art for use in sequence-specific alteration or modulation of gene expression to yield altered levels of an encoded polypeptide product. These advantages include lower effective siRNA polynucleotide concentrations, enhanced siRNA polynucleotide stability, and shorter siRNA polynucleotide oligonucleotide lengths relative to such other polynucleotides (e.g., antisense, ribozyme or triplex polynucleotides). By way of a brief background, "antisense" polynucleotides bind in a sequence-specific manner to target nucleic acids, such as mRNA or DNA, to prevent transcription of DNA or translation of the mRNA (see, e.g., U.S. Pat. No. 5,168,053; U.S. Pat. No. 5,190,931; U.S. Pat. No. 5,135,917; U.S. Pat. No. 5,087,617; see also, e.g., Clusel et al., 1993 *Nucl. Acids Res.* 21:3405-11, describing "dumbbell" antisense oligonucleotides). "Ribozyme" polynucleotides can be targeted to any RNA transcript and are capable of catalytically cleaving such transcripts, thus impairing translation of mRNA (see, e.g., U.S. Pat. No. 5,272,262; U.S. Pat. No. 5,144,019; and U.S. Pat. Nos. 5,168,053, 5,180,818, 5,116,742 and 5,093,246; U.S. Ser. No. 2002/193579). "Triplex" DNA molecules refers to single DNA strands that bind duplex DNA to form a colinear triplex molecule, thereby preventing transcription (see, e.g., U.S. Pat. No. 5,176,996, describing methods for making synthetic oligonucleotides that bind to target sites on duplex DNA). Such triple-stranded structures are unstable and form only transiently under physiological conditions. Because single-stranded polynucleotides do not readily diffuse into cells and are therefore susceptible to nuclease digestion, development of single-stranded DNA for antisense or triplex technologies often requires chemically modified nucleotides to improve stability and absorption by cells. siRNAs, by contrast, are readily taken up by intact cells, are effective at interfering with the expression of specific polynucleotides at concentrations that are several orders of magnitude lower than those required for either antisense or ribozyme polynucleotides, and do not require the use of chemically modified nucleotides.

Due to its advantages, RNAi has been applied as a target validation tool in research and as a potential strategy for in vivo target validation and therapeutic product development (Novina, C. D. and Sharp, P. A., *Nature,* 2004, 430:161-164). In vivo gene silencing with RNAi has been reported using viral vector delivery and high-pressure, high-volume intravenous (i.v.) injection of synthetic iRNAs (Scherr, M. et al. *Oligonucleotides,* 2003, 13:353-363; Song, E. et al. *Nature Med.,* 2003, 347-351). In vivo gene silencing has been reported after local direct administration (intravitreal, intranasal, and intrathecal) of siRNAs to sequestered anatomical sites in various models of disease or injury, demonstrating the potential for delivery to organs such as the eye, lungs, and central nervous system (Reich, S. J. et al. *Mol. Vis.,* 2003, 9:210-216; Zhang, X. et al. *J. Biol. Chem.,* 2004, 279:10677-10684; Dorn, G. et al. *Nucleic Acids Res.,* 2004, 32, e49). Silencing of endogenous genes by systemic administration of siRNAs has also been demonstrated (Soutschek, J. et al. *Nature,* 2004, 432:173-178).

BRIEF SUMMARY OF THE INVENTION

The present invention provides a method for reducing respiratory syncytial virus (RSV) gene expression within a subject by administering a polynucleotide that is specific for one or more target RSV genes such that the polynucleotide decreases RSV gene expression within the subject. The method of the invention is useful for treating RSV infections in human subjects and non-human subjects suffering from, or at risk for developing, RSV infections. The target gene may be any respiratory syncytial virus gene, or a portion thereof, such as NS1, NS2, N, P, M, SH, G, F, M2-1, M2-2, and L, or a portion of any of the foregoing. In some embodiments, the target gene is the RSV NS1 gene, or a portion thereof.

In a preferred embodiment of the method of the invention, the polynucleotides of the subject invention are administered locally or systemically to the subject's airway cells, such as respiratory epithelial cells, dendritic cells (DC), and/or monocytes.

In one aspect, the present invention is a method for reducing the expression of one or more RSV genes within a subject by administering an effective amount of polynucleotides that specifically target nucleotide sequence(s) within an RSV gene(s). In one embodiment, the method of the invention involves reducing expression of one or more RSV genes by administering a polynucleotide specific for the RSV gene, wherein the polynucleotide interferes with expression of the gene in a sequence-specific manner, to yield reduced levels of the gene product (the translated polypeptide).

In another aspect, the present invention provides a polynucleotide specific for one or more RSV genes, wherein the polynucleotide interferes with expression of the RSV gene(s). Preferably, the polynucleotide is a silencing double stranded ribonucleic acid (RNA) sequence, also called a small interfering RNA (siRNA) that causes degradation of the targeted RNA. Thus, in one embodiment, the polynucleotide is a double stranded ribonucleic aid (dsRNA) that reduces expression of the RSV gene. In one embodiment, the targeted nucleotide sequence is at least a portion of the RSV NS1 or NS2 genes. In a specific embodiment, the targeted nucleotide sequence is at least a portion of the RSV NS1 or NS2 genes, wherein a first strand of the dsRNA is substantially identical 19 to 49 consecutive nucleotides of NS1 or NS2, and a second strand of the dsRNA is substantially complementary to the first. In another embodiment, the polynucleotide is a double-stranded ribonucleic acid (dsRNA) comprising a first strand of nucleotides that is substantially identical to 19 to 25 consecutive nucleotides of RSV NS1 or NS2, and a second strand that is substantially complementary to the first strand.

In a specific embodiment, the siRNA comprises SEQ ID NO:1 or SEQ ID NO:2.

In another embodiment, the polynucleotide of the invention is a dsRNA comprising a first strand of nucleotides of at least 16 nucleotides sufficiently complementary to a target region of the RSV mRNA sequence to direct target-specific RNA interference (RNAi), and a second strand of nucleotides of at least 16 nucleotides substantially complementary to the first strand. In a further embodiment, the first strand is fully complementary to the target region of the mRNA sequence. In another embodiment, the dsRNA further comprises a loop formation comprising 4-11 nucleotides that connects the first and second strands. In a specific embodiment, the first and second strands each comprise 16, 17, 18, 19, 20, 21, 22, 23, 24, or 25 nucleotides. In another specific embodiment, the first and second strands each consist of 16, 17, 18, 19, 20, 21, 22, 23, 24, or 25 nucleotides.

In other embodiments, the polynucleotide of the invention is an antisense nucleic acid sequence (e.g., a single stranded oligonucleotide) that is complementary to a target region within the RSV mRNA, which binds to the target region and inhibits translation. The antisense oligonucleotide may be DNA or RNA, or comprise synthetic analogs of ribo-deoxynucleotides. Thus, the antisense oligonucleotide inhibits expression of the RSV gene. In one embodiment, the antisense oligonucleotide consists of 8 nucleotides complementary to contiguous nucleotides within the RSV mRNA. In other embodiments, the oligonucleotide has a length of 9, 10, 11, 12, 13, 14, 15, or 16 nucleotides.

In other embodiments, the polynucleotide of the invention is an RNA molecule having enzymatic activity (a ribozyme) that inhibits expression of the target RSV gene(s). In one embodiment, the ribozyme comprises a 5'-end flanking region having 4-50 nucleotides and being complementary to a 3'-end target region within the RSV mRNA; a stem-loop region, comprising a stem portion having 2-12 nucleotide pairs and a loop portion comprising at least 2 unpaired nucleotides; and a 3'-end flanking region having 4-50 nucleotides and being complementary to a 5' end target site on the substrate RNA.

The nucleic acid target of the polynucleotides (e.g., siRNA, antisense oligonucleotides, and ribozymes) of the invention may be any location within the RSV gene or transcript. Preferably, the nucleic acid target is located at a site selected from the group consisting of the 5' untranslated region (UTR), transcription start site, translation start site, and 3' UTR.

Other aspects of the invention include vectors (e.g., viral vectors. expression cassettes, plasmids) comprising or encoding polynucleotides of the subject invention (e.g., siRNA, antisense nucleic acids, and ribozymes), and host cells genetically modified with polynucleotides or vectors of the subject invention. In one embodiment, the vector comprises a polynucleotide and expression control sequences that direct production of a transcript that hybridizes under physiological conditions to a target region within the RSV mRNA. In one embodiment, the host cell is an epithelial cell, such as a respiratory epithelial cell, a dendritic cell (DC), or monocyte.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 1A shows an immunoblot of NS1 protein expression at 24 hours post-infection with rgRSV. FIG. 1B shows the results of flow cytometry analysis of rgRSV-positive A549 cells and Vero cells, respectively. FIGS. 1C and 1D show measurement of virus titer in A549 cells and Vero cells, respectively, using the plaque assay. Data are the averages of two independent experiments, $^{**}P<0.01$ when compared with control group.

FIGS. 2A-2E show that siNS1-mediated attenuation of RSV infection involves up-regulated expression of IFN-β and IFN-inducible genes in infected A549 cells. FIG. 2A shows an immunoblot of IFN-β protein expression at 24 hours post-infection with rgRSV. In order to quantitate the date from FIG. 2A, protein bands were scanned using the Scion image system (NIH) (FIG. 2B). FIG. 2C shows an immunoblot of the expression of IFN-inducible genes in three-hour post RSV-infected A549 cells. For each, the results of one experiment of two performed with similar results are shown. FIGS. 2D and 2E show that NS1 protein prevents nuclear import of IRF1 and STAT1. The nuclear localization of the IRF1 and STAT1 proteins in A549 cells was examined by indirect immunofluorescence using corresponding antibody. $^{*}P<0.05$ and $^{**}P<0.01$ relative to control. Results of one experiment of three representative experiments are shown.

FIG. 3A shows expression levels of IFN-α and IFN-β protein in RSV-infected DCs, treated with or without siNS1 were measured by ELISA assay. FIG. 3B shows the results of flow cytometric analysis of intracellular cytokine production in allogenic naïve CD4+ T cells after co-culture with RSV-infected DCs, treated with or without siNS1. Results shown are from one representative experiment of three repeats.

FIGS. 4A-4I show that siNS1 exhibits antiviral activity in vivo. FIG. 4A shows detection of NS1 gene expression using RT-PCR at 18 hours post-infection with rgRSV. FIG. 4B shows determination of viral lung titer using the plaque assay on A549 cells. *P<0.05 relative to control. Airway responsiveness to inhaled methacholine (MCh) was measured in mice infected with rgRSV following 2 days after prophylaxed with NG042-plasmid complex (FIG. 4C). The results are expressed as % Penh (enhanced pause) after inhalation of MCh relative to PBS. *P<0.05 compared to control. FIGS. 4D-4G show histology of lung sections of mice treated as in FIG. 4C (H&E staining). FIG. 4H shows detection of IFN-β gene expression in lung tissue using RT-PCR at 24 hours post-infection with rgRSV. To quantify data from FIG. 4H, DNA bands were scanned using the Scion image system (NIH) to quantify data from (FIG. 4I). *P<0.05 relative to control.

FIG. 5A shows measurement of viral lung titer in the mice prophylaxed at 2, 4 or 7 days prior to RSV infection using plaque assay on A549 cells. *P<0.05 relative to control. FIGS. 5B and 5C show intracellular cytokine production in spleen T cells in the mice at 5 day post secondary infection, which were prophylaxed at day-2, inoculated with rgRSV at day 1 and day 16. FIG. 5D shows measurement of viral lung titer from rechallenged mice ($1\times10^7$ PFU/mouse) at day 5 after secondary infection. *P<0.05 compared to control. Results of one experiment of two representative experiments are shown. FIG. 5E shows results of analysis of lung RSV titers at 5 days post-infection by plaque assay on A549 cells of mice treated with siRNA after different days of rgRSV-inoculation as indicated. *P<0.05 relative to control. FIGS. 5F-5I show histology (H&E staining) of lung sections of mice treated with NG042-siNS1s at day 2 post-infection.

FIGS. 6A and 6B show NS1 blocked activation of the type-1 IFN enhancer. Luciferase assays were performed to measure ISRE-mediated type-1 IFN activation using constructs that expressed either NS1/NS1a and/or siNS1.

BRIEF DESCRIPTION OF THE SEQUENCES

Figure 1A:
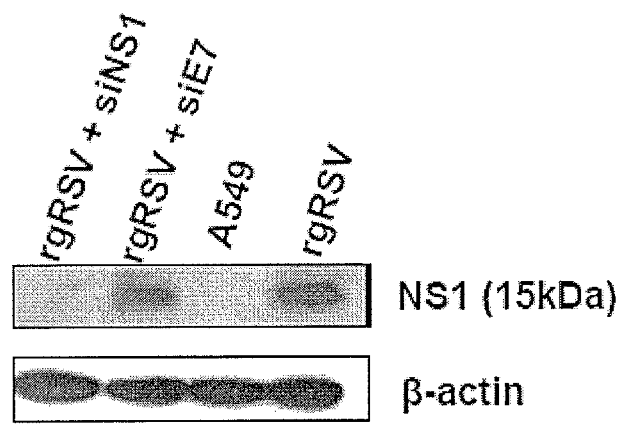
FIGS. 1A-1D demonstrate that siNS1 inhibits rgRSV infection.

SEQ ID NO:1 is the nucleotide sequence of the siRNA for RSV NS1, designated "siNS1".

SEQ ID NO:2 is the nucleotide sequence of the siRNA for RSV NS1, designated "siNS1a".

SEQ ID NO:3 is the nucleotide sequence of the siRNA for $HPV_{18}$ E7, designated "siE7".

SEQ ID NO:4 is the nucleotide sequence of the siRNA for type A Influenza virus PB2, designated "siPB2".

SEQ ID NO:5 is the nucleotide sequence of the siRNA for type A Influenza virus pUR, designated "siUR".

SEQ ID NO:6 is the IFN-β forward primer.

SEQ ID NO:7 is the IFN-β reverse primer.

SEQ ID NO:8 is the RSV-NS1 forward primer.

SEQ ID NO:9 is the RSV-NS1 reverse primer.

SEQ ID NO:10 is the RSV-F forward primer.

SEQ ID NO:11 is the RSV-F reverse primer.

SEQ ID NO:12 is the GAPDH forward primer.

SEQ ID NO:13 is the GAPDH reverse primer.

SEQ ID NO:14 is the nucleotide sequence of the human respiratory syncytial virus (HRSV), including genes NS1, NS2, N, P, M, SH, G, F, M2-1, M2-2, and L; NCBI accession no. M74568.

SEQ ID NO:15 is the nucleotide sequence of the bovine respiratory syncytial virus (BRSV); NCBI accession no. NC_001989.

DETAILED DESCRIPTION OF THE INVENTION

The present invention provides a method for reducing respiratiory syncytial virus (RSV) gene expression within a subject by administering a polynucleotide that is specific for one or more target RSV genes such that the polynucleotide decreases RSV gene expression within the subject. The method of the invention is useful for treating RSV infections in human subjects and non-human subjects suffering from, or at risk for developing, RSV infections. In addition, the method of the invention is useful for increasing type-I interferon within a subject, particularly when the subject is suffering from, or at risk for developing, a viral infection or inflammatory condition that reduces the subject's type-I interferon. Thus, the polynucleotides of the invention can counteract the interferon-lowering effects of such infections or conditions.

As used herein, the term "polypeptide" refers to any polymer comprising any number of amino acids, and is interchangeable with "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). Based on the nature of the invention, however, the term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference or otherwise reduce target gene expression.

As used herein, the term "operably-linked" or "operatively-linked" refers to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a siRNA will typically have its own operably-linked promoter sequence.

The term "vector" is used to refer to any molecule (e.g., nucleic acid, plasmid, or virus) used to transfer coding information (e.g., a polynucleotide of the invention) to a host cell. The term "expression vector" refers to a vector that is suitable for use in a host cell (e.g., a subject's cell) and contains nucleic acid sequences which direct and/or control the expression of exogenous nucleic acid sequences. Expression includes, but is not limited to, processes such as transcription, translation, and RNA splicing, if introns are present. The vectors of the present invention can be conjugated with chitosan or chitosan derivatives. Such chitosan conjugates can be administered to hosts according to the methods of the present invention. For example, polynucleotide chitosan nanoparticles (e.g., nanospheres) can be generated, as described by Roy, K. et al. (*Nat. Med.* 1999, 5:387). Chitosan allows increased bioavailability of the nucleic acid sequences because of protection from degradation by serum nucleases in the matrix and thus has great potential as a mucosal gene delivery system. Chitosan also has many beneficial effects, including anticoagulant activity, wound-healing properties, and immunostimulatory activity, and is capable of modulating immunity of the mucosa and bronchus-associated lymphoid tissue. In one embodiment of the present invention, the polynucleotides of the subject invention are conjugated with chitosan-derived nanoparticles.

As used herein, the terms "type-I INF", "type-1 interferon", "type-I interferon", and "type-1 INF" are used interchangeably to refer to interferon-alpha and/or interferon-beta.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA by the RNAi machinery or process. RSV "mRNA", "messenger RNA", and "transcript" each refer to single-stranded RNA that specifies the amino acid sequence of one or more RSV polypeptides. This information is translated during protein synthesis when ribosomes bind to the mRNA.

As used herein, the term "cleavage site" refers to the residues, e.g., nucleotides, at which RISC* cleaves the target RNA, e.g., near the center of the complementary portion of the target RNA, e.g., about 8-12 nucleotides from the 5' end of the complementary portion of the target RNA.

As used herein, the term "mismatch" refers to a basepair consisting of non-complementary bases, e.g., not normal complementary G:C, A:T or A:U base pairs.

As used herein, the term "isolated" molecule (e.g., isolated nucleic acid molecule) refers to molecules which are substantially free of other cellular material. or culture medium when produced by recombinant techniques, or substantially free of chemical precursors or other chemicals when chemically synthesized.

As used herein, the term "in vitro" has its art recognized meaning, e.g., involving purified reagents or extracts, e.g., cell extracts. The term "in vivo" also has its art recognized meaning, e.g., involving living cells in an organism, e.g., immortalized cells, primary cells, and/or cell lines in an organism.

A gene "involved in" or "associated with" a disorder includes a gene, the normal or aberrant expression or function of which affects or causes a disease or disorder or at least one symptom of the disease or disorder. For example, RSV NS1 protein has been found to have a significant role in RSV replication and immunity to RSV infection. Without being bound by theory, it has been found that the RSV NS1 protein down-regulates the interferon-signaling system by deactivation of STAT1, IRF1, and interferon-regulated gene expression, which are critical to suppressing interferon action. The polynucleotides, genetic constructs, pharmaceutical compositions, and methods of the invention are useful in decreasing expression of RSV genes, such as NS1 and/or NS2, in vitro or in vivo, consequently causing decreased production of the RSV protein and increased type I interferon (interferon alpha and/or interferon-beta). Thus, the polynucleotides, genetic constructs, pharmaceutical compositions, and methods of the invention are useful in the treatment of human or non-human animal subjects suffering from, or at risk of developing, disorders associated with impaired RSV infection and impaired interferon production.

The methods of the invention may include further steps. In some embodiments, a subject with the relevant condition or disease (e.g. RSV infection, disorders associated with RSV infection, or disorders associated with impaired interferon production) is identified, or a subject at risk for the condition or disease is identified. A subject may be someone who has not been diagnosed with the disease or condition (diagnosis, prognosis, and/or staging) or someone diagnosed with disease or condition (diagnosis, prognosis, monitoring, and/or staging), including someone treated for the disease or condition (prognosis, staging, and/or monitoring). Alternatively, the subject may not have been diagnosed with the disease or condition but suspected of having the disease or condition based either on patient history or family history, or the exhibition or observation of characteristic symptoms.

As used herein, an "effective amount" of polynucleotide (e.g., an siRNA, an antisense nucleotide sequence or strand, and/or a ribozyme, which selectively interferes with expression of the RSV gene(s)) is that amount effective to reduce expression of the target RSV gene and bring about the physiological changes desired in the cells to which the polynucleotide is administered in vitro (e.g., ex vivo) or in vivo. The term "therapeutically effective amount" as used herein, means that amount of polynucleotide (e.g., an siRNA, an antisense oligonucleotide, and/or a ribozyme, which selectively reduces expression of the RSV gene(s)), alone or in combination with another agent according to the particular aspect of the invention, that elicits the biological or medicinal response in cells (e.g., tissue(s)) that is being sought by a researcher, veterinarian, medical doctor or other clinician, which includes alleviation and/or prevention of the symptoms of the disease or disorder being treated. For example, a polynucleotide can be administered to a subject in combination with other agents effective for alleviating or preventing the symptoms of RSV infection, such as the gene expression vaccines disclosed in international publication WO 03/028759A1, which is incorporated by reference herein in its entirety.

Various methods of the present invention can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype. etc. can be determined prior to introducing a siRNA of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

RNA Interference

RNAi is an efficient process whereby double-stranded RNA (dsRNA, also referred to herein as siRNAs or ds siRNAs, for double-stranded small interfering RNAs) induces the sequence-specific degradation of targeted mRNA in animal and plant cells (Hutvagner and Zamore, *Curr. Opin. Genet. Dev.,* 12:225-232 (2002); Sharp, *Genes Dev.,* 15:485-490 (2001)). In mammalian cells, RNAi can be triggered by 21-nucleotide (nt) duplexes of small interfering RNA (siRNA) (Chiu et al., *Mol. Cell.,* 10:549-561 (2002); Elbashir et al., *Nature* 411:494-498 (2001)), or by micro-RNAs (miRNA), functional small-hairpin RNA (shRNA), or other dsRNAs which can be expressed in vivo using DNA templates with RNA polymerase III promoters (Zeng et al., *Mol. Cell.* 9:1327-1333 (2002); Paddison et al., *Genes Dev.* 16:948-958 (2002); Lee et al., *Nature Biotechnol.* 20:500-505 (2002); Paul et al., *Nature Biotechnol.* 20:505-508 (2002); Tuschl, T., *Nature Biotechnol.* 20:440-448 (2002); Yu et al., *Proc. Natl. Acad. Sci.* USA 99(9):6047-6052 (2002); McManus et al., RNA 8:842-850 (2002); Sui et al., *Proc. Natl. Acad. Sci.* USA 99(6):5515-5520 (2002)).

Accordingly, the invention includes such molecules that are targeted to RSV mRNAs encoding at least a portion of one or more of the eleven distinct RSV proteins: NS1, NS2, N, P, M, SH, G, F, M2-1, M2-2, and L. In a preferred embodiment, the siRNAs are targeted to RSV mRNA encoding at least a portion of the NS1 protein.

siRNA Molecules

The nucleic acid molecules or constructs of the invention include dsRNA molecules comprising 16-30 nucleotides, e.g., 16, 17, 18, 19, 20, 21, 22, 23, 24, 25, 26, 27, 28, 29, or 30 nucleotides, in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA of the RSV mRNA, and the other strand is identical or substantially identical to the first strand. The dsRNA molecules of the invention can be chemically synthesized, or can be transcribed in vitro from a DNA template, or in vivo from, e.g., shRNA. The dsRNA molecules can be designed using any method known in the art, for instance, by using the following protocol:

1. Beginning with the AUG start codon, look for AA dinucleotide sequences; each AA and the 3' adjacent 16 or more nucleotides are potential siRNA targets. Further, siRNAs with lower G/C content (35-55%) may be more active than those with G/C content higher than 55%. Thus, in one embodiment, the invention includes polynucleotides having 35-55% G/C content. In addition, the strands of the siRNA can be paired in such a way as to have a 3' overhang of 1 to 4, e.g., 2, nucleotides. Thus, in another embodiment, the polynucleotides can have a 3' overhang of 2 nucleotides. The overhanging nucleotides can be either RNA or DNA.

2. Using any method known in the art, compare the potential targets to the appropriate genome database (human, mouse, rat, etc.) and eliminate from consideration any target sequences with significant homology to other coding sequences for which reduced expression is not desired. One such method for such sequence homology searches is known as BLAST, which is available at the National Center for Biotechnology Information web site of the National Institutes of Health.

3. Select one or more sequences that meet your criteria for evaluation. Further general information regarding the design and use of siRNA can be found in "The siRNA User Guide," available at the web site of the laboratory of Dr. Thomas Tuschl at Rockefeller University.

4. Negative control siRNAs preferably have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The polynucleotides of the invention can include both unmodified siRNAs and modified siRNAs as known in the art. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions of the invention can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished by methods known in the art, e.g., using the methods of Lambert et al., *Drug Deliv. Rev.* 47(1): 99-112 (2001) (describes nucleic acids loaded to polyalkylcyanoacrylate (PACA) nanoparticles); Fattal et al., *J. Control Release* 53(1-3):137-43 (1998) (describes nucleic acids bound to nanoparticles); Schwab et al., *Ann. Oncol.* 5 Suppl. 4:55-8 (1994) (describes nucleic acids linked to intercalating agents, hydrophobic groups, polycations or PACA nanoparticles); and Godard et al., *Eur. J. Biochem.* 232(2):404-10 (1995) (describes nucleic acids linked to nanoparticles).

The nucleic acid molecules of the present invention can also be labeled using any method known in the art; for instance, the nucleic acid compositions can be labeled with a fluorophore, e.g. Cy3, fluorescein, or rhodamine. The labeling can be carried out using a kit, e.g., the SILENCER siRNA labeling kit (AMBION). Additionally, the siRNA can be radiolabeled, e.g., using $^{3}$H, $^{32}$P, or other appropriate isotope.

The dsRNA molecules of the present invention can comprise the following sequences as one of their strands, and the corresponding sequences of allelic variants thereof: SEQ ID NO:1 or SEQ ID NO:2.

Moreover, because RNAi is believed to progress via at least one single-stranded RNA intermediate, the skilled artisan will appreciate that ss-siRNAs (e.g., the antisense strand of a ds-siRNA) can also be designed as described herein and utilized according to the claimed methodologies.

siRNA Delivery for Longer-Term Expression

Synthetic siRNAs can be delivered into cells by methods known in the art, including cationic liposome transfection and electroporation. However, these exogenous siRNA generally show short-term persistence of the silencing effect (4 to 5 days in cultured cells), which may be beneficial in certain embodiments. To obtain longer term suppression of RSV gene expression and to facilitate delivery under certain circumstances, one or more siRNA duplexes, e.g., RSV ds siRNA, can be expressed within cells from recombinant DNA constructs. Such systems for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs; (Bagella et al., *J. Cell. Physiol.* 177:206-213 (1998); Lee et al. (2002), supra; Miyagishi et al. (2002), supra; Paul et al. (2002), supra; Yu et al. (2002), supra; Sui et al. (2002), supra). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence(s) under the control of a T7 promoter also make functional siRNAs when co-transfected into the cells with a vector expressing T7 RNA polymerase (Jacque (2002), supra). A single construct may contain multiple sequences coding for siRNAs, such as multiple regions of the RSV NS1 mRNA and/or other RSV genes, and can be driven, for example, by separate PolIII promoter sites.

Animal cells express a range of non-coding RNAs of approximately 22 nucleotides termed micro RNA (miRNAs) that can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra). Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., *Proc. Natl. Acad. Sci.* USA 99(22):14236-40 (2002)). In adult mice, efficient delivery of siRNA can be accomplished by the "high-pressure" delivery technique, a rapid injection (within 5 seconds) of a large volume of siRNA-containing solution into animal via the tail vein (Liu (1999), supra; McCaffrey (2002), supra; Lewis, *Nature Genetics* 32:107-108 (2002)). Nanoparticles and liposomes can also be used to deliver siRNA into animals.

Uses of Engineered RNA Precursors to Induce RNAi

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the RSV protein (such as RSV NS1 protein) encoded by that mRNA in the cell or organism. The RNA precursors are typically nucleic acid molecules that individually encode either one strand of a dsRNA or encode the entire nucleotide sequence of an RNA hairpin loop structure.

Antisense

An "antisense" nucleic acid sequence (antisense oligonucleotide) can include a nucleotide sequence that is complementary to a "sense" nucleic acid sequence encoding a protein, e.g., complementary to the coding strand of a double-stranded cDNA molecule or complementary to at least a portion of an RSV gene. The antisense nucleic acid sequence can be complementary to an entire coding strand of a target sequence, or to only a portion thereof (for example, the RSV NS1 gene and/or RSV NS2 gene, or a portion of either or both). In another embodiment, the antisense nucleic acid molecule is antisense to a "noncoding region" of the coding strand of a nucleotide sequence within the RSV gene. An antisense oligonucleotide can be, for example, about 7, 10, 15, 20, 25, 30, 35, 40, 45, 50, 55, 60, 65, 70, 75, 80, or more nucleotides in length.

An antisense nucleic acid sequence can be designed such that it is complementary to the entire RSV gene, but can also be an oligonucleotide that is antisense to only a portion of the RSV gene. For example, the antisense oligonucleotide can be complementary to the region surrounding the translation start site of the target mRNA, e.g., between the −10 and +10 regions of the target gene nucleotide sequence of interest. An antisense oligonucleotide sequence can be, for example, about 7, 10, 15, 20, 25, 30, 35, 40, 45, 50, 55, 60, 65, 70, 75, 80, or more nucleotides in length.

An antisense nucleic acid sequence of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid sequence also can be produced biologically using an expression vector into which a nucleic acid sequence has been subcloned in an antisense orientation (i.e., RNA transcribed from the inserted nucleic acid sequence will be of an antisense orientation to a target nucleic acid sequence of interest, described further in the following subsection).

The antisense nucleic acid molecules of the invention are typically administered to a subject (e.g., systemically or locally by direct injection at a tissue site), or generated in situ such that they hybridize with or bind to RSV mRNA to thereby inhibit expression of the viral protein. Alternatively, antisense nucleic acid molecules can be modified to target selected cells (such as respiratory epithelial cells, dendritic cells, and/or monocytes) and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, the antisense oligonucleotide of the invention is an alpha-anomeric nucleic acid molecule. An alpha-anomeric nucleic acid molecule forms specific double-stranded hybrids with complementary RNA in which, contrary to the usual beta-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.,* 215:327-330 (1987)).

Gene expression can be inhibited by targeting nucleotide sequences complementary to the regulatory region of the gene to form triple helical structures that prevent expression of the gene in target cells. See generally, Helene, C. *Anticancer Drug Des.* 6:569-84 (1991); Helene, C. *Ann. N.Y. Acad. Sci.* 660:27-36 (1992); and Maher, *Bioassays* 14:807-15 (1992). The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Ribozymes

Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme encoding nucleotide sequences can be introduced into cells through gene-delivery mechanisms known in the art. A ribozyme having specificity for RSV RNA can include one or more sequences complementary to the nucleotide sequence of at least a portion of one or more RSV mRNA (e.g., RSV NS1 mRNA), and a sequence having known catalytic sequence responsible for mRNA cleavage (see U.S. Pat. No. 5,093,246 or Haselhoff and Gerlach *Nature* 334:585-591 (1988)). For example, a derivative of a Tetrahymena L-19 IVS RNA can be constructed in which the nucleotide sequence of the active site is complementary to the nucleotide sequence to be cleaved in the RSV mRNA, such as RSV NS1 mRNA (see, e.g., Cech et al. U.S. Pat. No. 4,987,071; and Cech et al. U.S. Pat. No. 5,116,742). Alternatively, RSV mRNA encoding an RSV protein can be used to select a catalytic RNA having a specific ribonuclease activity from a pool of RNA molecules (see, e.g., Bartel, D. and Szostak, J. W. *Science* 261:1411-1418 (1993)).

Nucleic Acid Targets

The nucleic acid targets of the polynucleotides of the invention (e.g., antisense, RNAi, and ribozymes) may be any respiratory syncytial virus gene, or a portion thereof, such as NS1, NS2, N, P, M, SH, G, F, M2-1, M2-2, and L, or a portion of any of the foregoing. In some embodiments, the nucleic acid target is the RSV NS1 gene and/or NS2 gene, or a portion thereof. Optionally, a cocktail of polynucleotides specific for two or more RSV genes may be administered to a subject. Thus, for example, the polynucleotide cocktail may include polynucleotides having nucleic acid targets in, and thus capable of reducing expression of, two RSV genes, three RSV genes, four RSV genes, five RSV gene, six RSV genes, seven RSV genes, eight RSV genes, nine RSV genes, ten RSV genes, or eleven RSV genes (i.e., NS1, NS2, N, P, M, SH, G, F, M2-1, M2-2, and L). The nucleic acid target may be in any location within the RSV gene or transcript. Preferably, the nucleic acid target is located at a site selected from the group consisting of the 5' untranslated region (UTR), transcription start site, translation start site, and the 3' UTR.

The nucleic acid target may be located within a viral gene of strain A or strain B RSV. Preferably, the nucleic acid target is at least a portion of a non-structural RSV gene. More preferably, the nucleic acid target is at least a portion of an RSV gene encoding a non-structural protein (e.g., NS1 or NS2) that is common to both strain A RSV and strain B RSV. In a particularly preferred embodiment, the nucleic acid target is located within an RSV gene that normally down-regulates host interferon, such as the NS1 RSV gene. In another preferred embodiment, the nucleic acid target is located within the human RSV NS1 or NS2 gene at a site selected from the group consisting of the 5' untranslated region (UTR), transcription start site, translation start site, and the 3' UTR.

The nucleic acid target may be located within a human RSV (HRSV) gene (NCBI accession no. M745568, which is incorporated herein by reference in its entirety) or an ortholog thereof, such as a bovine RSV (BRSV) gene (NCBI accession no. NC_001989, which is incorporated herein by reference in its entirety). For treating and/or preventing RSV infection within a particular subject, the polynucleotide selected for administration to the subject is preferably one targeted to a viral gene for which the subject is within the virus's normal host range. For example, for treating and/or preventing RSV infection within a human subject, the nucleic acid target is preferably located within a human RSV gene, or the nucleic acid target has sufficient homology with the human RSV gene, so as to reduce expression of the human RSV gene. For example, for treating and/or preventing RSV infection within cattle, the nucleic acid target is preferably located within a bovine RSV gene, or the nucleic acid target has sufficient homology with the bovine RSV gene, so as to reduce expression of the bovine RSV gene.

The mRNA sequence of the RSV protein can be any ortholog of the mRNA sequence, such as sequences substantially identical to those of RSV viruses having a non-human host range (e.g., bovine RSV).

The term "ortholog" as used herein refers to a sequence which is substantially identical to a reference sequence. The term "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%. 91%, 92%, 93%, 94%, 95%, 96%, 97%, 98% or 99% identity are defined herein as substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, at least 60%, at least 70%, at least 80%, at least 90%, at least 95%, or at least 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman and Wunsch (*J. Mol. Biol.* 48:444-453 (1970)) algorithm, which has been incorporated into the GAP program in the GCG software package (available at the official Accelrys web site), using either a Blossum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at the official Accelrys web site), using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*CABIOS,* 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other orthologs, e.g., family members or related sequences. Such searches can be performed using the NBLAST and XBLAST programs (version 2.0) of Altschul, et al. *J. Mol. Biol.* 215:403-10 (1990). BLAST nucleotide searches can be performed with the NBLAST program, score=100, word length=12, to obtain nucleotide sequences homologous to known RSV DNA and RNA sequences. BLAST protein searches can be performed with the XBLAST program, score=50, word length=3, to obtain amino acid sequences homologous to known RSV polypeptide products. To obtain gapped alignments for comparison purposes, Gapped BLAST can be utilized as described in Altschul et al., *Nucleic Acids Res.* 25:3389-3402 (1997). When utilizing BLAST and Gapped BLAST programs, the default parameters of the respective programs (e.g., XBLAST and NBLAST) can be used (see the National Center for Biotechnology Information web site of the National Institutes of Health).

Orthologs can also be identified using any other routine method known in the art, such as screening a cDNA library, e.g., using a probe designed to identify sequences that are substantially identical to a reference sequence.

Pharmaceutical Compositions and Methods of Administration

The polynucleotides of the subject invention (e.g., siRNA molecules, antisense molecules, and ribozymes) can be incorporated into pharmaceutical compositions. Such compositions typically include the polynucleotide and a pharmaceutically acceptable carrier. As used herein, the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Formulations (compositions) are described in a number of sources that are well known and readily available to those skilled in the art. For example, *Remington's Pharmaceutical Sciences* (Martin E. W., Easton Pa., Mack Publishing Company, $19^{th}$ ed., 1995) describes formulations which can be used in connection with the subject invention.

A pharmaceutical composition is formulated to be compatible with its intended route of administration. Examples of routes of administration include parenteral, e.g., intravenous, intradermal, subcutaneous, oral (e.g., inhalation), nasal, topical, transdermal, transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL (BASF, Parsippany, N. J.) or phosphate buffered saline (PBS). In all cases, the composition must be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. Isotonic agents, for example, sugars, polyalcohols such as manitol, sorbitol, sodium chloride can also be included in the composition. Prolonged absorption of the injectable compositions can be brought about by including in the composition an agent that delays absorption, such as aluminum monostearate or gelatin.

Sterile injectable solutions can be prepared by incorporating the active compound (e.g., a polynucleotide of the invention) in the required amount in an appropriate solvent with one or a combination of ingredients enumerated above, as required, followed by filtered sterilization. Generally, dispersions are prepared by incorporating the polynucleotide into a sterile vehicle, which contains a basic dispersion medium and the required other ingredients from those enumerated above. In the case of sterile powders for the preparation of sterile injectable solutions, suitable methods of preparation include vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the polynucleotides can be delivered in the form of drops or an aerosol spray from a pressured container or dispenser that contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, drops, or suppositories. For transdermal administration, the active compound (e.g., polynucleotides of the invention) are formulated into ointments, salves, gels, or creams, as generally known in the art.

The pharmaceutical compositions can also be prepared in the form of suppositories (e.g., with conventional suppository bases such as cocoa butter and other glycerides) or retention enemas for rectal delivery.

The polynucleotides can also be administered by transfection or infection using methods known in the art, including but not limited to, the methods described in McCaffrey et al., *Nature* 418(6893):38-39 (2002) (hydrodynamic transfection); Xia et al., *Nature Biotechnol.* 20(10):1006-10 (2002) (viral-mediated delivery); or Putnam, *Am. J. Health Syst. Pharm.* 53(2):151-160 (1996), erratum at *Am. J. Health Syst. Pharm.* 53(3):325 (1996).

The polynucleotides can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al., *Clin. Immunol. Immunopathol.* 88(2):205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996). Preferably, the polynucleotides of the invention are administered to the subject such that an effective amount are delivered to the respiratory epithelial cells, DC, and/or monocytes within the subject's airway, resulting in an effective amount of reduction in RSV gene expression (e.g., reduction in RSV NS1 and/or NS2 gene expression).

In one embodiment, the polynucleotides are prepared with carriers that will protect the polynucleotide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers.

These can be prepared according to methods known to those skilled in the art, for example, as described in U.S. Pat. No. 4,522,811.

Preferably, the polynucleotides of the subject invention (e.g., compositions containing them) are administered locally or systemically such that they are delivered to the cells of the airway, such as airway epithelial cells, which line the nose as well as the large and small airways. It is also preferred that the polynucleotides of the invention be delivered to dendritic cells and/or monocytes.

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the method of the invention, the therapeutically effective dose can be estimated initially from cell culture assays. A dose can be formulated in animal models to achieve a circulating plasma concentration range that includes the IC50 (i.e., the concentration of the test composition which achieves a half-maximal inhibition of symptoms) as determined in cell culture. Such information can be used to more accurately determine useful doses in humans. Levels in plasma can be measured, for example, by high performance liquid chromatography.

The compositions of the invention can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a polynucleotide can include a single treatment or can include a series of treatments.

Mammalian species that benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. As used herein. the terms "subject" and "host" are used interchangeably and intended to include such human and non-human mammalian species. Likewise, in vitro methods of the present invention can be carried out on cells of such mammalian species. Host cells comprising exogenous polynucleotides of the invention may be administered to the subject, and may, for example, be autogenic (use of one's own cells), allogenic (from one person to another), or transgenic or xenogenic (from one species to another), relative to the subject.

The polynucleotides of the invention can be inserted into genetic constructs, e.g., viral vectors, retroviral vectors, expression cassettes, or plasmid viral vectors, e.g., using methods known in the art, including but not limited to those described in Xia et al., (2002). supra. Genetic constructs can be delivered to a subject by, for example, inhalation, orally, intravenous injection, local administration (see U.S. Pat. No. 5,328,470) or by stereotactic injection (see, e.g., Chen et al., *Proc. Natl. Acad. Sci.* USA 91:3054-3057 (1994)). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

The polynucleotides of the invention can also include small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., *Science* 296:550-553 (2002); Lee et al., (2002), supra; Miyagishi and Taira, *Nature Biotechnol.* 20:497-500 (2002); Paddison et al. (2002), supra; Paul (2002), supra; Sui (2002) supra; Yu et al. (2002), supra.

SiRNAs of the invention may be fused to other nucleotide molecules, or to polypeptides, in order to direct their delivery or to accomplish other functions. Thus, for example, fusion proteins comprising a siRNA oligonucleotide that is capable of specifically interfering with expression of one or more RSV genes may comprise affinity tag polypeptide sequences, which refers to polypeptides or peptides that facilitate detection and isolation of the polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al., (*Bio/Technology* 6:1204, 1988), or the XPRESS epitope tag (INVITROGEN, Carlsbad, Calif.). The affinity sequence may be a hexa-histidine tag as supplied, for example, by a pBAD/His (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

The present invention also relates to vectors and to constructs that include or encode polynucleotides, of the present invention (e.g., siRNA), and in particular to "recombinant nucleic acid constructs" that include any nucleic acid such as a DNA polynucleotide segment that may be transcribed to yield RSV mRNA-specific siRNA polynucleotides according to the invention as provided above; to host cells which are genetically engineered with vectors and/or constructs of the invention and to the production of siRNA polynucleotides, polypeptides, and/or fusion proteins of the invention, or fragments or variants thereof, by recombinant techniques. siRNA sequences disclosed herein as RNA polynucleotides may be engineered to produce corresponding DNA sequences using well-established methodologies such as those described herein. Thus, for example, a DNA polynucleotide may be generated from any siRNA sequence described herein, such that the present siRNA sequences will be recognized as also providing corresponding DNA polynucleotides (and their complements). These DNA polynucleotides are therefore encompassed within the contemplated invention, for example, to be incorporated into the subject invention recombinant nucleic acid constructs from which siRNA may be transcribed.

According to the present invention, a vector may comprise a recombinant nucleic acid construct containing one or more promoters for transcription of an RNA molecule, for example, the human U6 snRNA promoter (see, e.g., Miyagishi et al., *Nat. Biotechnol.* 20:497-500 (2002); Lee et al., *Nat. Biotechnol.* 20:500-505 (2002); Paul et al., *Nat. Biotechnol.* 20:505-508 (2002); Grabarek et al., *BioTechniques* 34:73544 (2003); see also Sui et al., *Proc. Natl. Acad. Sci.* USA 99:5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for an RSV sequence may be transcribed under the control of a single promoter such that the siRNA polynucleotide forms a hairpin molecule (Paul et al., supra). In such an instance, the complementary strands of the siRNA specific sequences are separated by a spacer that comprises at least four nucleotides, but may comprise at least 5, 6, 7, 8, 9, 10, 11, 12, 14, 16, 94 18 nucleotides or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., *Science* 296:550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

Polynucleotides of the invention can be expressed in mammalian cells, yeast, bacteria, or other cells under the control of appropriate promoters, providing ready systems for evaluation of RSV-specific polynucleotides that are capable of interfering with expression of RSV genes, as provided herein. Appropriate cloning and expression vectors for use with prokaryotic and eukaryotic hosts are described, for example, by Sambrook, et al., Molecular Cloning: A Laboratory Manual, Third Edition, Cold Spring Harbor, N.Y., (2001).

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (2001 Molecular Cloning, Third Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control (i.e., regulatory) sequence (e.g., a promoter or a regulated promoter) to direct mRNA synthesis. Representative examples of such expression control sequences include LTR or SV40 promoter, the *E. coli* lac or tip, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter, or regulated promoter, operably linked to a polynucleotide of the invention is described herein.

As noted above, in certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters that may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above. A tissue-specific promoter allows preferential expression of the polynucleotide in a given target tissue (such as tissue of the respiratory tract), thereby avoiding expression in other tissues. For example, to express genes specifically in the heart, a number of cardiac-specific regulatory elements can be used. An example of a cardiac-specific promoter is the ventricular form of MLC-2v promoter (see, Zhu et al., *Mol. Cell. Biol.* 13:4432-4444, 1993; Navankasattusas et al., *Mol. Cell. Biol.* 12:1469-1479, 1992) or a variant thereof such as a 281 bp fragment of the native MLC-2v promoter (nucleotides −264 to +17, Genebank Accession No. U26708). Examples of other cardiac-specific promoters include alpha myosin heavy chain (Minamino et al., *Circ. Res.* 88:587-592, 2001) and myosin light chain-2 (Franz et al., *Circ. Res.* 73:629-638, 1993). Endothelial cell gene promoters include endoglin and ICAM-2. See Velasco et al., *Gene Ther.* 8:897-904, 2001. Liver-specific promoters include the human phenylalanine hydroxylase (PAH) gene promoters (Bristeau et al., *Gene* 274:283-291, 2001), hB1F (Zhang et al., *Gene* 273:239-249, 2001), and the human C-reactive protein (CRP) gene promoter (Ruther et al., *Oncogene* 8:87-93, 1993). Promoters that are kidney-specific include CLCN5 (Tanaka et al., *Genomics* 58:281-292, 1999), renin (Sinn et al., *Physical Genomics* 3:25-31, 2000), androgen-regulated protein, sodium-phosphate cotransporter, renal cytochrome P-450, parathyroid hormone receptor and kidney-specific cadherin. See *Am. J. Physiol. Renal Physiol.* 279:F383-392, 2000. An example of a pancreas-specific promoter is the pancreas duodenum homeobox 1 (PDX-1) promoter (Samara et al., *Mol. Cell. Biol.* 22:4702-4713, 2002). A number of brain-specific promoters may be useful in the invention and include the thy-1 antigen and gamma-enolase promoters (Vibert et al., *Eur. J. Biochem.* 181:33-39, 1989), the glial-specific glial fibrillary acidic protein (GFAP) gene promoter (Cortez et al., *J. Neurosci. Res.* 59:39-46, 2000), and the human FGF1 gene promoter (Chiu et al., *Oncogene* 19:6229-6239, 2000). The GATA family of transcription factors have promoters directing neuronal and thymocyte-specific expression (see Asnagli et al., *J. Immunol.* 168:4268-4271, 2002).

In a specific embodiment of the expression vector (e.g., viral or non-viral) of the subject invention, the promoter is H1 or U6. Preferably, the expression vector (e.g., viral or non-viral) of the subject invention includes a tissue-specific promoter such as surfactant protein B (SPB) and/or a steroid response element (SRE), such as the glucocorticoid response element (GRE) (Bohinski, R. J. et al. *J. Biol. Chem.*, 1993, 268(15):11160-11166; Bohinski, R. J. et al. *Mol. Cell. Biol.*, 1994, 14(9):5671-5681; Itani, O A. et al. *Am. J. Physiol. Endocrinol. Metab.*, 2002, 283(5):E971-E979; Huynh, T. T. et al. *J. Endocrinol.*, 2002, 172(2):295-302). Such regulatory sequences are particularly useful where selective expression of the operably linked polynucleotide within the subject's airway is desired and/or where expression of the polynucleotide only in the presence of steroids is desired. For example, it may desirable to administer a polynucleotide of the subject invention operably linked to a steroid response element, wherein a steroid is co-administered to the subject as combination therapy.

In another aspect, the present invention relates to host cells containing the above described recombinant constructs. Host cells are genetically engineered/modified (transduced, transformed or transfected) with the vectors and/or expression constructs of this invention that may be, for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells according to the present invention include, but need not be limited to, bacterial cells, such as *E. coli, Streptomyces, Salmonella typhimurium*; fungal cells, such as yeast; insect cells, such as *Drosophila* S2 and *Spodoptera* Sf9; animal cells, such as CHO, COS or 293 cells; adenoviruses; plant cells, or any suitable cell already adapted to in vitro propagation or so established de novo.

Various mammalian cell culture systems can also be employed to produce polynucleotides of the invention from recombinant nucleic acid constructs of the present invention. The invention is therefore directed in part to a method of producing a polynucleotide, such as a siRNA, by culturing a host cell comprising a recombinant nucleic acid construct that comprises at least one promoter operably linked to a polynucleotide of the invention that is specific for at least one RSV gene. In certain embodiments, the promoter may be a regulated promoter as provided herein, for example a tetracycline-repressible promoter. In certain embodiments, the recombinant expression construct is a recombinant viral expression construct as provided herein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAE-Dextran mediated transfection, or electroporation (Davis et al., 1986 Basic Methods in Molecular Biology), or other suitable technique.

The expressed polynucleotides may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

As used herein, the terms "administer", "apply", "treat", "transplant", "implant", "deliver", and grammatical variations thereof, are used interchangeably to provide polynucleotides of the subject invention (e.g., vectors containing or encoding polynucleotides of the subject invention) to target cells in vitro or in vivo, or provide genetically modified (engineered) cells of the subject invention to a subject ex vivo.

As used herein, the term "co-administration" and variations thereof refers to the administration of two or more agents simultaneously (in one or more preparations), or consecutively. For example, one or more types of polynucleotides of the invention (e.g., vectors containing or encoding polynucleotides of the subject invention) can be co-administered with other agents. Optionally, the method of the invention includes co-administration of a polynucleotide of the invention and an additional therapeutic agent such as an anti-viral agent or vaccine (e.g., an anti-RSV agent or gene expression vaccine).

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence" includes more than one such sequence. A reference to "a cell" includes more than one such cell.

The terms "comprising", "consisting" of and "consisting essentially of" are defined according to their standard meaning. The terms may be substituted for one another throughout the instant application in order to attach the specific meaning associated with each term.

Materials and Methods

Virus and Cell Lines.

A549, Vero cell line and RSV strain A2 were obtained from the American Type Culture Collection (ATCC, Rockville, Md.). Recombinant rgRSV which encodes green-fluorescent protein was kindly supplied by Dr. Mark E. Peeples (Hallak, L. K. et al. *Virology,* 2000, 271:264-275).

Plasmid Constructs.

The nucleotide sequence for each siRNA is as follows:

```
siNS1:
                                        (SEQ ID NO: 1)
5'-GGCAGCAATTCATTGAGTATGCTTCTCGAAATAAGCATACTCAATGA

ATTGCTGCCTTTTTG-3';

siNS1a:
                                        (SEQ ID NO: 2)
5'-GTGTGCCCTGATAACAATATTCAAGAGATATTGTTATCAGGGCACAC

TT-TTTTG-3';

siE7:
                                        (SEQ ID NO: 3)
5'-GAAAACGATGAAATAGATGTTCAAGAGACATCTATTTCATCGTTTTC

T-TTTTT-3';

siPB2:
                                        (SEQ ID NO: 4)
5'-GGCTATATTCAATATGGAAAGAACTCGAGTTTTGTTCTTTCCATAT

T-GAATATAGCCTTTTTG-3';
and

siUR:
                                        (SEQ ID NO: 5)
5'-GGTCACGATCAGAATACTTCGCTCGAGCGAAG-TATTCTGATCGTGA

CCCTTTTTTG-3'.
```

Each pair of oligos was inserted into pSMWZ-1 plasmid at appropriate sites respectively, to generate the corresponding siRNA for RSV NS1, $HPV_{18}$ E7, type A Influenza virus PB2 and pUR.

DNA Transfection and Virus Infection.

Cells were transfected with siNS1 or controls (siE7, siPB2 or siUR) using LIPOFECTAMINE 2000 reagent (INVITROGEN, Carlsbad, Calif.). 24 hours later, cells were infected with rgRSV or RSV at appropriate multiplicity of infection. pEGFP plasmid (STRATAGENE, La Jolla, Calif.) was used for measurement of transfection efficiency.

Isolation of DCs from Human Peripheral Blood and Measurement of IFNs in Supernatants of Infected DCs.

Monocytes purified from PBMCs using monocyte isolation Kit II (MILTENYI BIOTEC, Auburn, Calif.) were seeded into six-well culture plates supplemented with 200 ng/ml IL-4 and 50 ng/ml GM-CSF (BD-PHARMINGEN, San Diego, Calif.) and cultured for 6 to 7 days for plasmid transfection and infection with RSV. Expression level of IFNs in the supernatants was assayed by IFN-α Multi-Species ELISA Kit and IFN-β ELISA kit (PBL Biomedical Laboratories, Piscataway, N.J.).

Analysis of Intracellular Cytokine Production in T Cells.

Human naïve CD4+ T cells ($1\times10^6$ cells/well) purified using CD4+ T cell isolation kit (MILTENYI BIOTEC, Auburn, Calif.) from umbilical cord blood were co-cultured with irradiated monocyte-derived DCs (30 Gy) ($1\times10^5$ cells/well) in 24-well plates for 6 days with additional culture for 8 days in the presence of recombinant hIL2 (10 ng/ml); mice spleen T cells purified using mouse T-cell enrichment column kit (R & D Systems, Minneapolis, Minn.) were cultured in 6-well plates for 4 days. Finally, cells were stimulated with PMA (50 ng/ml) and ionomycin (500 ng/ml) (SIGMA, Saint Louis, Mo.) for 6 hours in the presence of GOLGISTOP (PHARMINGEN, San Diego, Calif.) and then fixed and stained using CD8 or CD4 mAb (BD BIOSCIENCES, San Diego, Calif.) for flow cytometry analysis.

Immunofluorescence.

A549 cells were fixed with 2% paraformaldehyde, permeabilized with 0.1% Triton X-100, and blocked with 3% Donkey serum in PBS containing 1% Glycerin for 60 minutes. Cells were next incubated with IRF1 antibody (SANTA CRUZ BIOTEC, Santa Cruz, Calif.) or pSTAT1 (Ser 727, Upstate, Charlottesville, Va.), respectively, and then with ZENON ALEXA FLUOR 488 (MOLECULAR PROBES, Eugene, Oreg.). The slides were visualized by immunofluorescence microscopy.

Plaque Assay.

10-fold serial dilutions of the supernatants were added to a monolayer of A549 cells and the medium in each well of six-well culture plates was replaced by an agarose-containing overlay (2×DMEM, 10% FBS, 1% low melting point agarose (GIBCO BRL, Rockville, Md.). The plates were incubated at 37° C. for 5 days. Afterwards, 1% neutral red (SIGMA, Saint Louis, Mo.) was added and the plaques were counted 48 hours later.

Microarray Assays.

Total RNAs were extracted by RNASE (QIAGEN RNeasy Kit). 10 μg of total RNAs were used to prepare cDNA. Gene expression was analyzed with GENECHIP Human Genome U95Av2 probe array (AFFYMETRIX, Santa Clara, Calif.) according to the manufacture's protocol (Expression Analysis Technical Manual). Data analysis was performed with Microarray Suite 5.0 (MAS 5.0).

Protein Expression Analysis by Western Blotting.

Transfected A549 cells were infected with rgRSV (MOI=1). The whole cell lysates were electrophoresed on 12% polyacrylamide gels and the proteins were transferred to PVDF membranes (BIO-RAD, Hercules, Calif.). The blot was incubated separately with RSV polyclonal antibody (AB1128, CHEMICON Int. Temecula, Calif.), STAT1, pSTAT1 (Tyr 701), STAT2, IRF1, IRF3, IRF7, ISGF-3γ and IFN-β (SANTA CRUZ BIOTECH, Santa Cruz, Calif.), pSTAT1 (Ser 727, Upstate, Charlottesville, Va.) or MxA antibody (Dr. Otto Haller, Germany). Immunoblot signals were developed by SUPER SIGNAL ULTRA chemiluminescent reagent (PIERCE, Rockford, Ill.).

Studies in Mice.

Animal studies were approved by the University of South Florida and VA Hospital Institutional Animal Care and Utilization Committee. All animal studies were blinded to remove investigator bias. Six-week old female BALB/c mice (n=8 per group) purchased from Charles River Laboratory (Frederick, Md.) were administered with plasmid with NG042 (TRANSGENEX NANOBIOTECH Inc., Tampa) intranasally (10 μg/mouse of plasmid) prior to or after rgRSV inoculation ($5\times10^6$ PFU/mouse). The pulmonary function was evaluated at day 4 post-infection as described previously (Kumar, M. et al. *Hum. Gene Ther.,* 2002, 13:1415-1425). Finally, all mice were sacrificed the next day. The RSV titer was determined by plaque assay from the lung homogenate (n=8), and histological sections from lungs (n=8) were stained with hematoxylin and eosin. RT-PCR analysis in the lung tissue was performed using the following primers. IFN-β: Forward, 5'-ATAAG-CAGCTC-CAGCTCCAA-3' (SEQ ID NO:6), Reverse, 5'-CTGTCTGCTGGTGGAGTTCA-3' (SEQ ID NO:7); RSV-NS1: Forward, 5'-ATGGGGTGCAATTCATTGAG-3' (SEQ ID NO:8), Reverse, 5'-CAGGGCACACTTCACT-GCT-3' (SEQ ID NO:9); RSV-F: Forward, 5'-TGCAGTG-CAGTTAGCAAAGG-3' (SEQ ID NO:10), Reverse, 5'-TCTGGCTCGATTGTTTGTTG-3' (SEQ ID NO:11); and GAPDH: Forward, 5'-CCCTTCATTGACCTCAACT-3' (SEQ ID NO:12), Reverse, 5'-GACGCCAGTG-GACTCCA-3' (SEQ ID NO:13). PCR products were visualized by gel electrophoresis and quantified by densitometry.

Statistical Analysis.

Pairs of groups were compared by Student t test. Differences between groups were considered significant at $p<0.05$. Data for all measurements are expressed as means±SD.

TABLE 1

IFN-inducible genes change more than 6-fold in RSV-infected A549 cells.

| Genebank accession number | Gene | Function | Fold change (FC)[3] | Comparison[b] rgRSV | Comparison[b] rgRSV + siNS1 |
|---|---|---|---|---|---|
| NM_007315 | STAT1 | signal transducer and activator of transcription 1 | 6 | D | I |
| NM_002198 | IRF1 | interferon regulatory factor 1 | 6 | D | I |
| NM_001571 | IRF3 | interferon regulatory factor 3 | 6 | NC | I |
| NM_004030 | IRF7 | interferon regulatory factor 7 | 6 | D | I |
| NM_006084 | IRF9 | ISGF3G (p48) | 6 | D | I |
| NM_005531 | IFI16 | interferon gamma-inducible protein 16 | 6 | D | I |
| NM_005532 | IFI27 | interferon, alpha-inducible protein 27 | 6 | D | I |
| NM_006332 | IFI30 | interferon gamma-inducible protein 30 | 6 | D | I |
| BF338947 | IFITM2 | interferon induced transmembrane protein 2 | 6 | D | I |
| AL121994 | 1-8U | contains a pseudogene similar to IFITM3 (interferon induced transmembrane protein 3, STSs and GSSs | 6 | D | I |
| BE049439 | IFI44 | interferon-induced, hepatitis C-associated microtubular aggregate protein (44 kD) | 8 | D | I |
| NM_004509 | IFI41 | SP110 nuclear body protein (interferon-induced protein 75, 52 kD) | 6 | D | I |
| NM_003641 | PTS | 6-pyruvoyltetrahydropterin synthase-interferon induced transmembrane protein 1 (9-27) (IFITM1) | 6 | D | I |
| NM_005101 | ISG15 | interferon alpha-inducible protein (clone IFI-15K) | 6 | D | I |
| NM_002201 | ISG20 | interferon stimulated gene (20 kD) (ISG20) | 6 | D | I |
| NM_022147 | IFRG28 | 28 kD interferon responsive protein | 8 | D | I |
| NM_002176 | IFNB1 | interferon beta 1, fibroblast | 8 | D | I |
| NM_002462 | MxA | interferon-regulated resistance GTP-binding protein | 6 | D | I |
| NM_002463 | MxB | interferon-regulated resistance GTP-binding protein | 7 | D | I |
| NM_016817 | OAS2 | 2'-5'-oligoadenylate synthetase 2, 69/71 kDa | 8 | D | I |
| NM_003733 | OASL | 2'-5'-oligoadenylate synthetase-like | 6 | D | I |
| NM_016816 | OAS1 | 2',5'-oligoadenylate synthetase 1, 40/46 kDa | 6 | D | I |
| NM_006187 | OAS3 | 2'-5'-oligoadenylate synthetase 3, 100 kDa | 6 | D | I |
| NM_001550 | IFRD1 | interferon-related developmental regulator 1 | 6 | D | I |
| NM_001547 | IFIT2 | interferon-induced protein with tetratricopeptide repeats 2 | 8 | D | I |

[a] Value for the fold change in expression calculated by the Microarray Suite 5.0 (MAS 5.0) program.

[b] The data were compared to arrays of rgRSV-infected A549 cells either with or without siNS1 treatment. I, increased; NC, not changed; D, decreased.

It should be understood that the examples and embodiments described herein are for illustrative purposes only and that various modifications or changes in light thereof will be suggested to persons skilled in the art and are to be included within the spirit and purview of this application.

Example 1 siNS1 Inhibition of rgRSV Infection

Figure 1B:
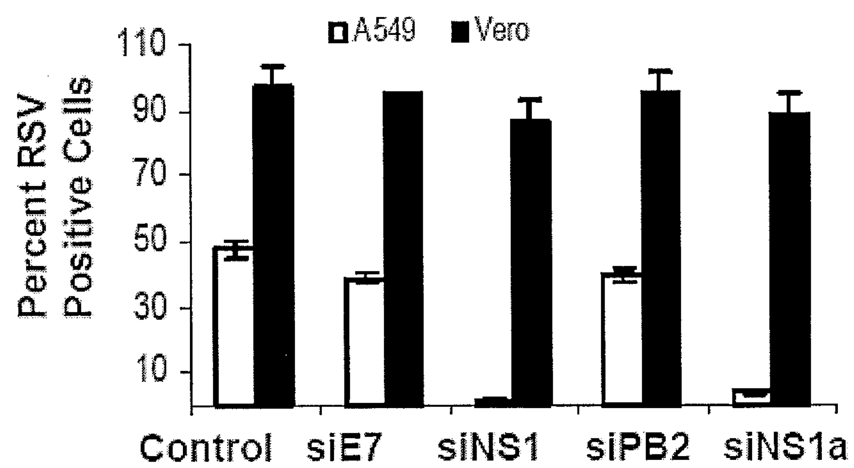
Figure 1C:
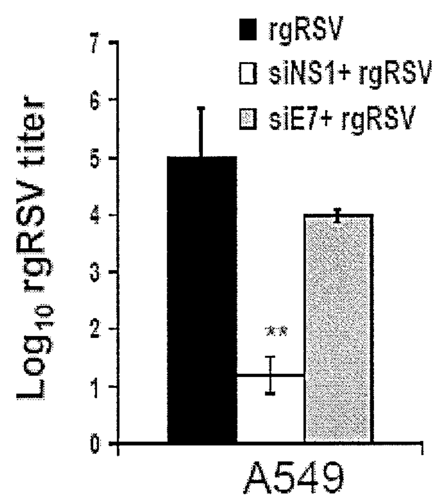
Figure 1D:
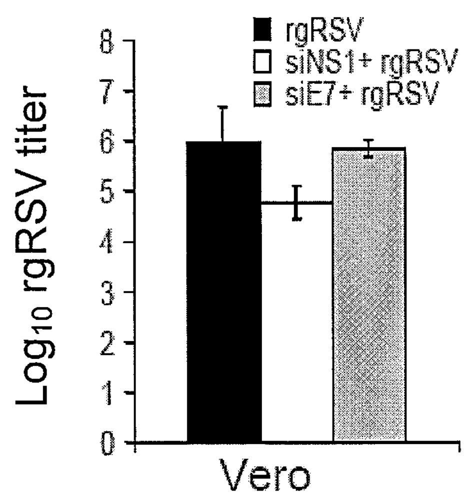

Two different siRNA oligos for RSV NS1, siNS1 and siNS1a, HPV18E7 (siE7) and Influenza virus PB2 (siPB2) were designed and cloned into the pSMWZ-1 vector (Zhang, W. et al. *Genetic Vaccines Ther.,* 2004, 2:8-12). Analysis of EGFP expression in A549 cells co-transfected with pEGFP and siNS1/1a, siE7 or siPB2 demonstrates that none of siRNAs silence the EGFP gene (data not shown). Immunoblotting results show that pre-transfection of A549 cells with siNS1, but not siE7, significantly reduces the expression of NS1 proteins (FIG. 1A), but not that of other viral proteins (data not shown). To test whether siNS1 attenuates virus infection, A549 cells and type-1 IFN deficient (Mosca, J. D. and Pitha, P. M. *Mol. Cell. Biol.,* 1986, 6:2279-2283) Vero cells were transfected with the siNS1, siNS1a, or control siRNAs, and then infected with rgRSV (Hallak, L. K. et al. *Virology,* 2000, 271:264-275). The results of flow cytometry show a significant decrease in the percentage of cells expressing EGFP. In marked contrast to A549, siNS1/1a does not decrease viral replication in Vero cells compared to controls (FIG. 1B). Furthermore, plaque assays for RSV titers in culture supernatants indicate that siNS1 significantly decreases rgRSV titer compared to controls ($P<0.01$) in A549 cells (FIG. 1C), but not Vero cells (FIG. 1D). Plaque assays using siNS1a gave results similar to those from siNS1 (not shown). Together, these results indicate that siNS1 attenuates RSV infection in a gene-specific fashion, and this attenuation may involve NS1-modulation of the type-1 IFN pathway.

Example 2

Mechanism of siNS1-Mediated Upregulation of Type-1 IFN Pathway

The finding that RSV infection of A549 cells, but not Vero cells, is affected by siNS treatment suggests a role of NS1 protein in the promotion of RSV infection by inhibiting the type-1 IFN pathway.

To verify whether NS1 decreases the amount of type-1 IFN, the expression of IFN-β was examined by immunoblotting. The results show that A549 cells transfected with siNS1 or siNS1a, upon RSV infection, produce significantly increased amounts of IFN-β, compared to the different controls, including totally unrelated siRNA with no homology to mammalian genes (siUR), (FIGS. 2A and 2B).

Figure 2C:
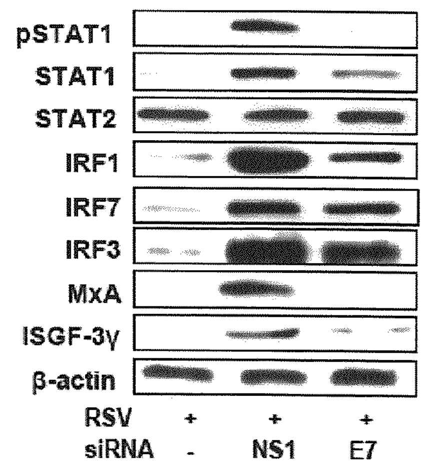

To further examine the role of NS1 in regulating the IFN pathway, RNAs from control and siNS1-transduced cells were isolated and subjected to microarray analyses. The results show that siNS1 treatment increased the expression (≥6 fold-change) of 25 IFN-inducible genes compared to rgRSV infection alone (Table 1), and the expression of a number of altered genes was investigated by western blotting. The results show that the pSTAT1 (Ser 727), STAT1, IRF1, IRF3, ISGF-3γ and MxA proteins were up-regulated after siNS1 inhibition (FIG. 2C).

Figure 2D:
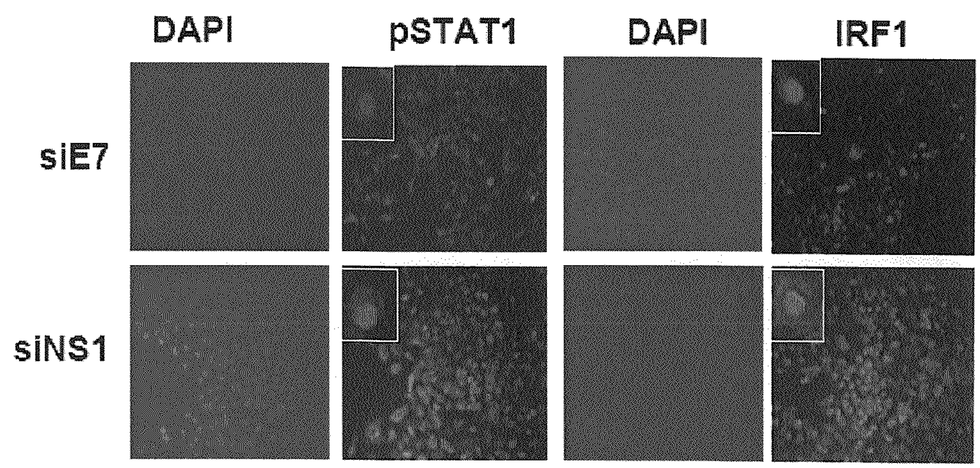
Figure 2E:
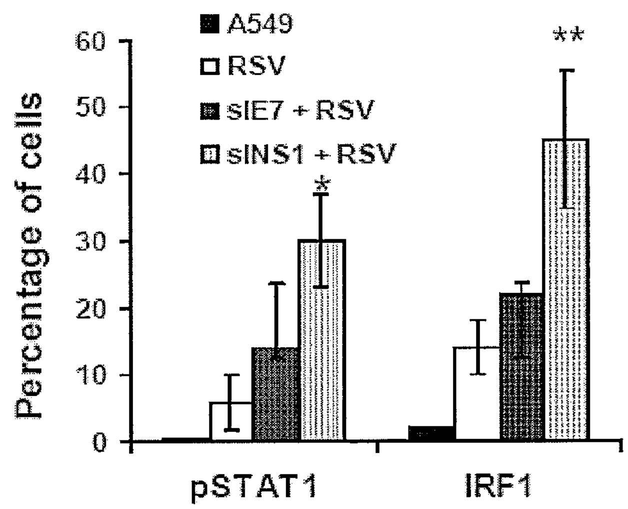

To determine whether NS1 affects STAT1 and IRF1 translocation in A549 cells, transfected-cells were infected with wild-type RSV (MOI=0.1), fixed 3 hours later, permeabilized, and stained with appropriate antibody. Cells treated with siNS1 showed significantly higher nuclear localization of phospho-STAT1 and IRF1 compared to controls (FIGS. 2D and 2E), suggesting that the NS1 protein blocks trafficking of these proteins into the nucleus.

Example 3

Silencing NS1 Polarizes Human Dendritic Cells Toward a Th1-Promoting phenotype

Figure 3A:
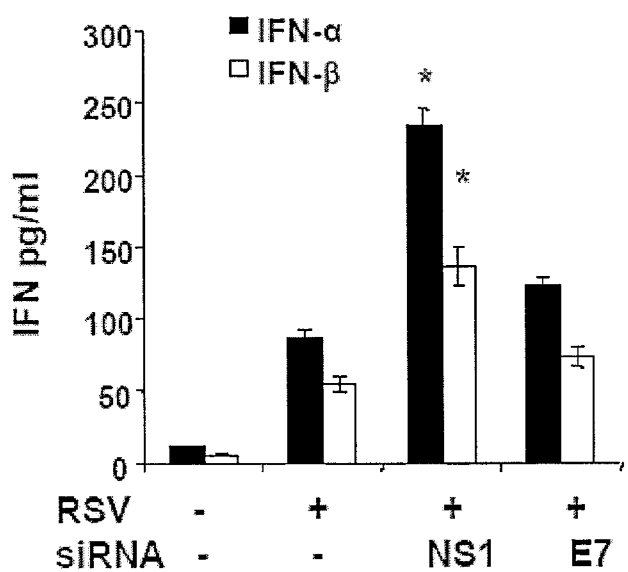
FIGS. 3A and 3B Effect of siNS1 on human DCs and naïve CD4+ T cells.
Figure 3B:
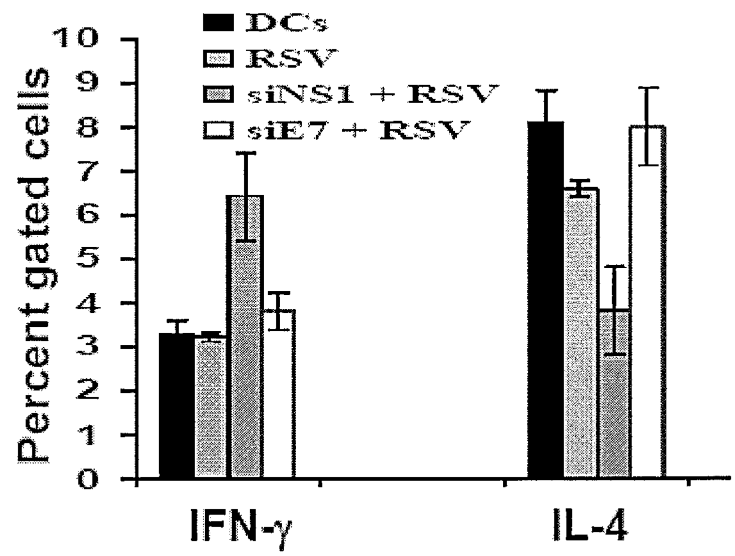

Monocytes isolated from human peripheral blood were cultured with requisite cytokines to test whether siNS1 expression affects RSV-infected DC activity. Thus, the IFN-α and IFN-β concentrations were measured in the supernatants from cultured, infected, monocyte-derived DCs transfected with siNS1 or control. The data show that siNS1 treatment induces a significantly higher production of both type-1 IFNs in infected DCs than it does in controls (FIG. 3A). Furthermore, to assess the effect of siNS1-treated DCs on T-cell function, allogenic naïve CD4+ T cells were co-cultured with RSV-infected DCs treated with or without siNS1. The results of intracellular cytokine staining showed an increase in IFN-γ and a decrease in IL-4 secretion in naïve CD4+ T cells for siNS1-treated, RSV-infected DCs, compared with controls (FIG. 3B).

Example 4

Figure 4A:
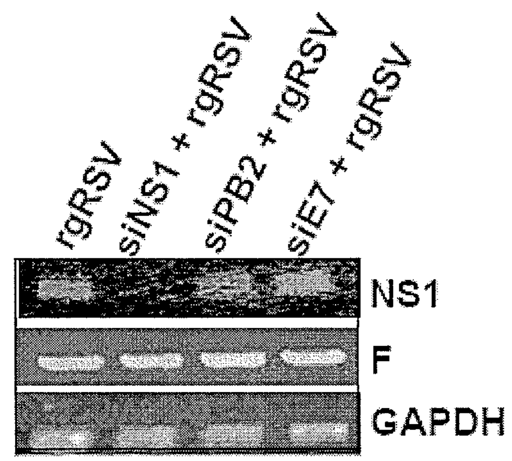
Figure 4B:
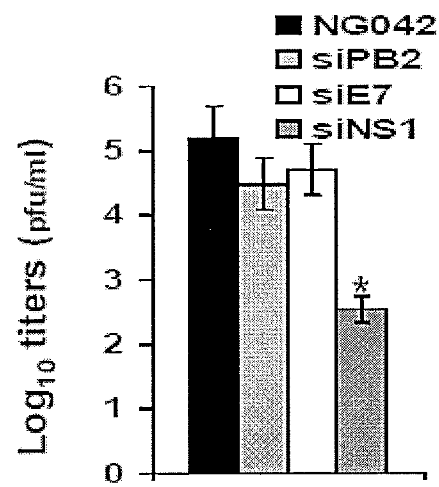
Figure 4C:
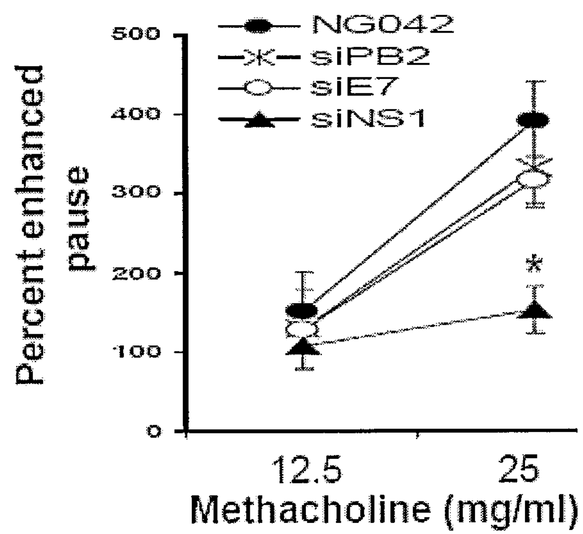
Figure 4D:
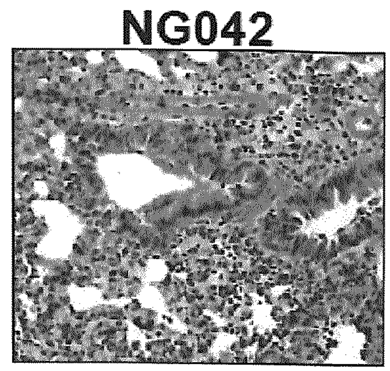
Figure 4E:
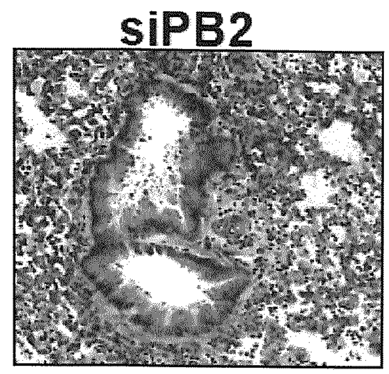
Figure 4F:
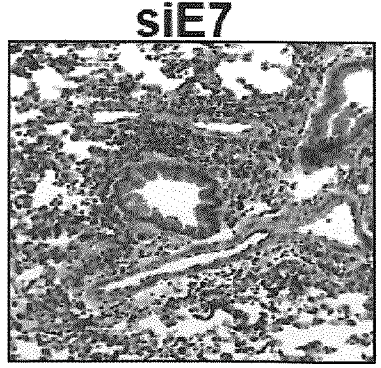
Figure 4G:
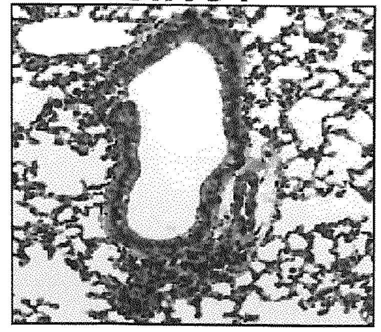

Prophylaxis with Nanoparticle-Complexed siNS1 (Nano-siNS1) Significantly Attenuates RSV Infection and Pulmonary Pathology in Mice To determine whether siNS1 exerts an antiviral response in vivo in BALB/c mice, the siNS1 plasmid was complexed with a nanochitosan polymer, referred to as Nanogene 042 (NG042). The nanoparticles were administered as a nasal drop 2 days before viral inoculation. NS1 expression in the lungs (n=6) of mice was assayed by RT-PCR 18 hours post-infection. As revealed by RT-PCR data, siNS1 significantly knocked down expression of the RSV-NS1 gene but not of the RSV-F gene (FIG. 4A). The viral titer in supernatants of homogenized lungs (n=8) was also indicated to significantly decrease in the siNS1-treatment infected mice compared to controls ($P<0.05$) (FIG. 4B). These mice (n=8) were challenged with methacholine at day 4 following rgRSV infection. RSV-infected mice showed a greater than 400% increase in enhanced pause (Penh) values compared to baseline and a 300% increase compared to the siNS1 group (FIG. 4C). Mice treated with siNS1 show significantly lower AHR than that of untreated mice ($P<0.05$) and exhibit a significant reduction in pulmonary inflammation, as evidenced by decreases in the goblet cell hyperplasia of the bronchi and in the number of infiltrating inflammatory cells in the interstitial regions compared to controls (FIGS. 4D-4G).

To assess IFN-β expression in the lung tissue, total RNAs were extracted from the indicated group (n=6), with siRNA treatment 2 days before RSV inoculation, and assayed by RT-PCR 24 hours post-infection. The results showed that knockdown of the RSV NS1 gene significantly increased IFN-β expression in the lung compared to controls ($P<0.05$) (FIGS. 4H and 4I). Examination of IFN-α level in the BAL fluid by ELISA revealed a 2-fold increase in IFN concentration in siNS1-treated mice compared to control mice (not shown).

Example 5

Potential of Nano-siNS1 for Prophylaxis and Treatment of RSV Infection

Figure 5A:
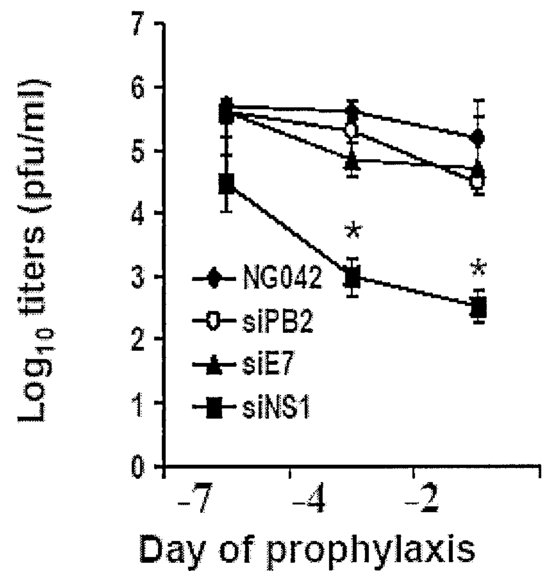
FIGS. 5A-5I show prophylactic and therapeutic potential of NG042-siNS1.
Figure 5B:
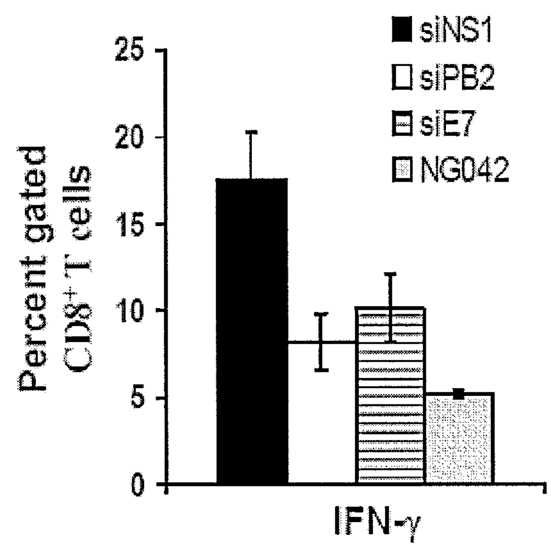
Figure 5C:
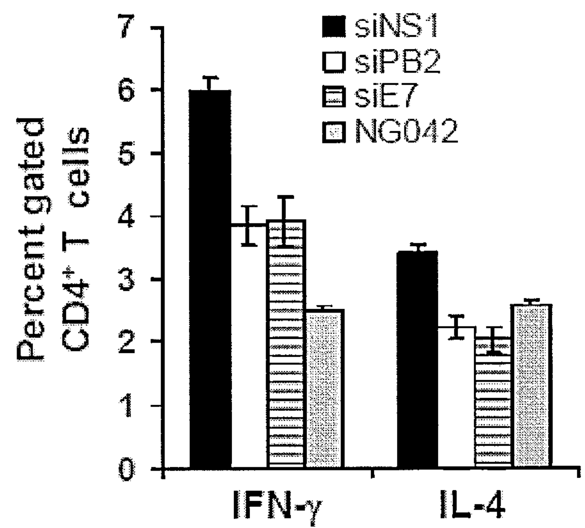
Figure 5D:
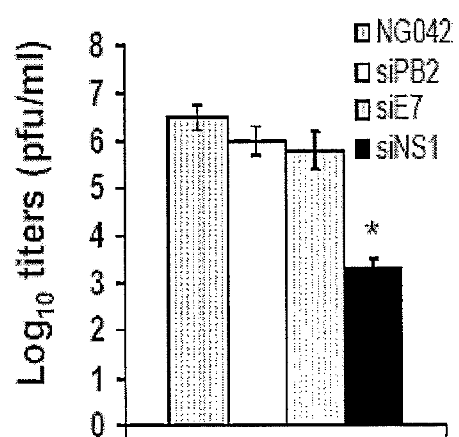

To investigate the persistence of siNS1 prophylaxis, mice were treated with NG042-siNS1 complex for 2, 4 and 7 days prior to viral inoculation. Analysis of viral titers 5 days post-infection shows that the siNS1 effect can last for at least 4 days, although treatment at day-7 still lowers viral titer by 1 log compared to control (FIG. 5A). To test whether prophylactic blocking of NS1 activity can induce anti-RSV immunity and provide protection from re-infection, mice were administered with NG042-siNS1, inoculated with RSV ($5\times10^6$ PFU/mouse) 2 days after and re-inoculated with RSV ($10^7$ PFU/mouse) after 16 days. Cellular immunity induced by RSV at 5 days post-infection was examined in these mice by intracellular cytokine staining of splenocytes for IFN-γ and IL-4. Splenocytes of mice treated with NG042-siNS1 show an increase in IFN-γ production in both CD4+ and CD8+ T cells and also increases in IL-4 production in CD4+ T cells compared with controls (FIGS. 5B and 5C). Also, examination of virus titer following secondary infection revealed that mice treated with NG042-siNS1 show a significant decrease in the viral titers compared to control mice (FIG. 5D). Thus, prophylaxis with siNS1 enhances cellular immunity and attenuates the secondary RSV infection.

Figure 5E:
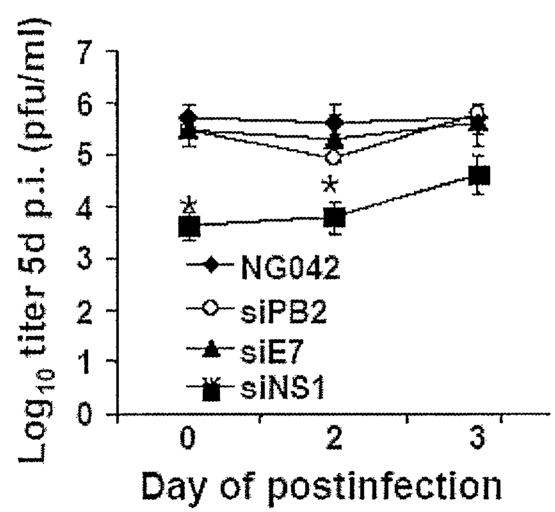
Figure 5F:
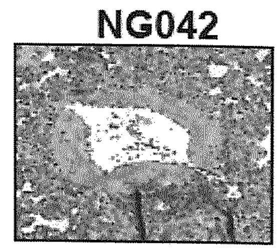
Figure 5G:
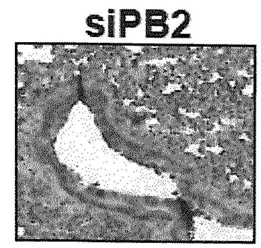
Figure 5H:
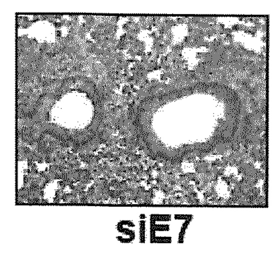
Figure 5I:
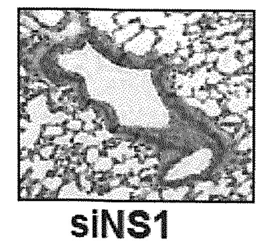

To test the therapeutic potential of NG042-siNS1, mice were administered with NG042-siNS1 at day 0 along with RSV inoculation or at day 2 or 3 post-infection. The results show that mice treated the same day as inoculation or at 2 days post-RSV infection exhibit a significantly lower viral titer compared to controls ($P<0.05$) (FIG. 5E). Treatment with NG042-siNS1 at 3 days post-inoculation also decreases virus titer, albeit marginally. Further, lung sections of mice treated with NG042-siNS1 after 2 days of RSV infection were examined and the results show that treated mice exhibit a significant decrease in lung inflammation (goblet hyperplasia and infiltration of inflammatory cells compared to control mice (FIGS. 5F-5I).

Example 6

RSV NS1 Protein Blocks Type-1 IFN Signaling

Figure 6A:
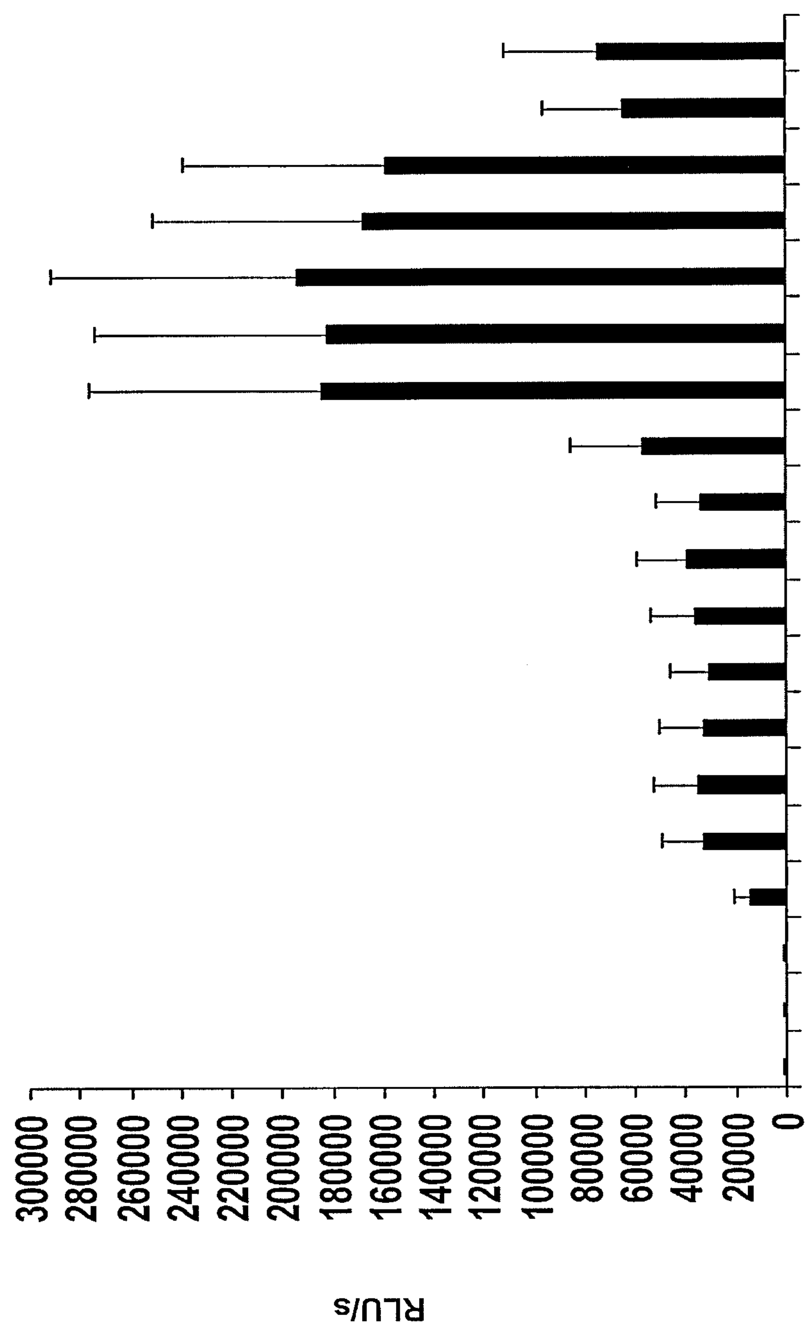

To test the effect NS1 protein has on the induction of type-1 IFN, pISRE-luc reporter plasmid (with IFN-stimulated response element plus an inducible cis-enhancer element) was used to co-transfect A549 cells with indicated plasmid (FIGS. 6A and 6B). A549 cells ($1\times10^6$ cells) were co-transfected with 1 μg of either pISRE-luc or pCIS-CK negative control plasmid (STRATAGENE, La Jolla, Calif.) along with different indicated plasmid. At 24 hours post-transfection, the cells were treated with poly(I):poly(C) (AMERSHAM, Piscataway N.J.) (0.2 μg) for 18 h and then subjected to a luciferase assay by using the luciferase assay system (PROMEGA, Madison, Wis.) according to the manufacturer's instructions. Luciferase assays showed that specific knockdown of NS1 expression increased luciferase activity significantly compared to other controls, indicating that NS1 protein blocks type-1 IFN signaling.

In this experiment, siNS1/1a induced significantly higher amounts of IFN compared to siE7 or siPB2 (the same vector as siNS1), indicating that NS1 is involved in antagonizing type-1 IFN. In addition, the transfection of Vero cells either with siE7 or siPB2 did not attenuate viral infection, and luciferase assays also indicated that even the same empty vector induced almost the same amount of luciferase activity as siRNAs alone, suggesting that the plasmid itself might induce transfected A549 cells to up-regulate certain IFN-inducible genes. This could account for the finding that siE7 or siPB2 somewhat reduced rgRSV production in vitro or in vivo and that siE7 and siPB2, even the empty vector (data not shown) induced IFN-β in A549 cells.

The data disclosed herein describes, for the first time, the significant role of NS1 in RSV replication and immunity to RSV infection. These studies demonstrate that the NS1 protein down-regulates the IFN-signaling system by deactivation of STAT1, IRF1, and IFN-regulated gene expression, which are critical to suppressing IFN action. Furthermore, the results reveal the potential for nanoparticles encapsulating siNS1 for the prophylaxis and treatment of RSV infections.

Vector-driven de novo expression of siRNA to attenuate RSV infection has not been reported heretofore, although antisense oligonucleotide-mediated attenuation of RSV infection in African green monkeys has been reported (Leaman, D. W. et al. *Virology,* 2002, 292:70-77). However, the potential of this approach remains uncertain as the effects of these oligos were measured at the very early stage of infection, i.e., 30 minutes post-RSV challenge. Mechanistically, both antisense and siRNA work at the post-transcriptional level to reduce the expression of the target gene. The antisense oligonucleotides accumulate in the nucleus and may alter splicing of precursor mRNA (Fisher, T. L. et al. *Nucleic Acids Res.,* 1993, 21:3857-3865; Kole, R. and Sazani, P. *Curr. Opin. Mol. Ther.,* 2001, 3:229-234). In contrast, siRNAs exert function in the cytoplasm (Billy, E. et al. *Proc. Natl. Acad. Sci. USA,* 2001, 98:14428-14433), which is the site of RSV replication. Also, intracellular expression from RNA polymerase III promoters enables the production of stably expressing siRNA in the cell with sustained knockdown of the target, and hence, lower concentrations are needed to achieve levels of knockdown that are comparable to those from antisense reagents.

A major finding of this report is the demonstration that DNA-vector driven siNS1 expression is capable of significantly attenuating the RSV infection of human epithelial cells, which are the primary targets of RSV replication. A549 epithelial cells were used, as they are similar to cultured primary airway cells in terms of their susceptibility to RSV (Arnold, R. et al. *Immunology,* 1994, 82:126-133). The transfection efficiency of the construct using plasmid pEGFP was 43.21% and 49.62% in A549 cells and Vero cells, respectively. Despite this, the siNS1 plasmid inhibited rgRSV production by 90-97%, which is consistent with a 2 to 3 log decrease in RSV titers. Furthermore, two different siRNA constructs targeting NS1 showed almost identical results. Although the mechanism of the siNS1-mediated decrease in viral titers was not investigated, it may be attributed to the fact that NS1, located at the 3' end of the viral genome, acts as a common early stage promoter for the initiation of both replication and transcription (Atreya, P. L. et al. *J. Virol.,* 1998, 72:1452-1461). These results are consistent with reports that suggest that deletion of NS1 strongly attenuates RSV infection in vivo (Jin, H. et al. *Virology,* 2000, 273:210-208; Teng, M. N. et al. *J. Virol.,* 2000, 74:9317-9321; Murphy, B. R. and Collins, P. L. *J. Clin. Invest.,* 2002, 110:21-27).

The mechanism of siNS1-induced attenuation of viral replication was investigated. To establish that the antiviral effects of siNS1 are due to modulation of the IFN-pathway, Vero cells that lack the type-1 IFN genes were utilized and compared with A549 cells. Whereas A549 cells exhibited significant siNS1— or siNS1a-induced decreases in rgRSV-infected cell numbers and virus titers, no effect of siNS1/1a was seen in Vero cells. Also, in parallel studies, Vero cells co-transfected with pEGFP and siEGFP, not siNS1, showed significant knock down (91.68%) of EGFP gene expression (not shown). These results show a definitive role of siNS1/1a in the attenuation of RSV replication and implicate the type-1 IFN pathway in this process.

IFNs drive a cascade of intracellular signaling, resulting in the expression of a large number of interferon-stimulated genes (ISGs) that exert the pleiotropic effects of IFN, including interference with viral replication and modulation of the host immune response (Stark, G. R. et al. *Annu. Rev. Biochem.,* 1998, 67:227-264). The level of expression of IFN-inducible genes in infected A549 cells treated with siNS1 was significantly altered, as revealed by the microarray data. IRF3 and MxA expression were up-regulated after NS1 inhibition, in agreement with a previous report on bovine RSV (Bossert, B. et al. *J. Virol.,* 2003, 77:8661-8668), although STAT2 levels were not changed. In addition, expression of STAT1, IRF1, and ISGF-3γ, were significantly up-regulated in our studies, compared to control. IRF1 may play a critically important role in human RSV infection since it functions as a transcriptional activator (Barnes, B. et al. *J Interferon Cytokine Res.,* 2002, 22:59-71) and binds to the positive regulatory domain 1 (PRD1) of the IFN-β promoter (Harada, H. et al. *Cell,* 1989, 58:729-739) and to the IFN-stimulated response element (ISRE) of IFN-stimulated genes (Pine, R. et al. *Mol. Cell. Biol.,* 1990, 10:2448-2457). ISGF-3γ encodes a protein-interaction function that allows recruitment of STAT1 and STAT2, their translocation from the cytoplasm to the nucleus, and initiation of transcription of IFN-stimulated genes (ISGs) (Stark, G. R. et al. *Annu. Rev. Biochem.,* 1998, 67:227-264). Furthermore, results show that both the IRF1 and phospho-STAT1 proteins translocate into the nucleus of infected A549 cells through knockdown of the NS1 protein, which suggests that NS1 targets activation of STAT1 and IRF1.

An important finding of this study is that siNS1/1a induced significantly higher amounts (a three-fold increase) of IFN-β compared to controls including siE7 or siPB2 (the same vector as siNS1) and the totally unrelated siRNA, indicating that NS1 is involved in antagonizing type-1 IFN. These results are in agreement with the increases in IFN production observed with NS1/NS2-deleted human RSV infection (Bossert, B. and Conzelmann, K. K. *J. Virol.,* 2002, 76:4287-4293; Bossert, B. et al. *J. Virol.,* 2003, 77:8661-8668; Schlender, J. et al. *J. Virol.,* 2000, 74:8234-8242; Spann, K. M. et al. *J. Virol.,* 2004, 78:4363-4369). It is noteworthy, however, that compared to RSV-infected cells, cells transfected with either the vector plasmid or with siRNA targeting different viral antigens or a totally unrelated siRNA and showed a slight increase of IFN-β production following RSV infection. This may be attributed to plasmid-driven siRNA-induced IFN-stimulated genes, including PKR and OAS (Sledz, C. A. et al. *Nat. Cell. Biol.,* 2003, 5:834-839; Bridge, A. J. et al. *Nat. Genet.,* 2003, 34:263-264), to CpG motifs (amp$^r$ gene) present in the vector plasmid that activate innate immunity via binding to TLR9 (Sato, Y. et al. *Science,* 1996, 273:352-354), or to the U6 promoter-vector, which induces a higher frequency of interferon-stimulated genes compared to lentiviral H1 vectors (Pebernard, S, and Iggo, R. D. *Differentiation,* 2004, 72:103-111). The vector or control siRNA-induced IFN production also up-regulates certain IFN-inducible genes, particularly STAT1 and IRF1 and 3, which may account for the finding that siE7 or siPB2 reduced rgRSV production in vitro by about 1 log. However, siNS1 induces a significantly higher level of expression of these ISGs, including MxA and ISGF-3γ, and, in addition, promotes phosphorylation of STAT1.

Whereas epithelial cells are the major target cells in which the virus replicates, monocytes and dendritic cells play a role in generating anti-RSV immunity. Monocytes play a role in the pathophysiology of RSV bronchiolitis (Bont, L. et al. *J. Infect. Dis.,* 2000, 181:1772-1775), and they represent a pool of circulating precursors capable of differentiating into DCs that are able to present pathogen-derived peptides to naïve T cells. NS1 appears to decrease type-1 IFN production in DCs, presumably affecting their state of activation and antigen presentation. The result of these studies demonstrate that RSV infection decreases the capacity of DCs to induce IFN-γ in naïve T cells (Bartz, H. et al. *Immunology,* 2003, 109:49-57), which might cause the delayed RSV-specific immune response and permit multiple RSV re-infections. Thus, infected DCs treated with siNS1 produce much more type-1 IFN and also drive naïve CD4+ T cells toward Th1-type lymphocytes that generate more IFN-γ and less IL-4.

A significant result of the data disclosed herein is that a new generation of polynucleotide agents can be used to reduce RSV gene expression in a subject, resulting in treatment and protection from RSV infection. For example, oligomeric nano-size chitosan particles, NG042, can be used for de novo expression of siNS1 in the lung tissues of a subject, resulting in treatment and protection from RSV infection. NG042 shows higher transduction efficiency and induces less inflammation compared to classical high molecular weight chitosan (data not shown). The results of studies on the prophylactic potential of NG042-siNS1 indicate that siNS1 induces significant protection from rgRSV infection, infection-induced inflammation, and airway reactivity, and the protective effect lasted for at least 4 days. Furthermore, even a single-dose prophylaxis with NG042-siNS1 significantly attenuates mice from re-infection with a higher dose of RSV 16 days after primary infection. The precise mechanism of enhanced protection is unknown, but it is likely that knockdown of the NS1 gene augments anti-RSV host immunity via enhanced IFN production and thereby prevents mice from RSV re-infection. In addition, NG042-siNS1 also attenuates the established RSV infection. Thus, the antiviral treatment decreased viral titer in the lung, improved pulmonary function, and attenuated pulmonary inflammation in rgRSV-infected mice. Together, these data support the prophylactic and therapeutic potential of siNS1 nanoparticles.

In conclusion, together these data demonstrate that NS1 promotes virus infection of human epithelial and dendritic cells by inhibiting type-1 IFN pathway. Therefore, treatment with NG042-siNS1 either prior to or after RSV infection significantly attenuates RSV infection and infection-induced pulmonary pathology in mice. Thus, the siNS1 nanoparticles may prove to be a potent, new prophylactic and/or therapeutic agent against RSV infection in humans.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A method for reducing the expression of a respiratory syncytial virus (RSV) gene and RSV viral titer in a human subject, comprising administering a vector to airway cells in the subject, wherein the subject does not have an RSV infection at the time the vector is administered, wherein the vector comprises a nucleic acid sequence encoding a short interfering RNA (siRNA) targeted to a target nucleic acid sequence within the RSV NS1 gene or RSV NS1 transcript, and wherein the vector is administered in an effective amount to reduce expression of the RSV NS1 gene or NS1 transcript in the airway cells and reduce RSV titer in the subject.

2. The method of claim 1, wherein the vector is a viral vector.

3. The method of claim 1, wherein the vector is a non-viral vector.

4. The method of claim 1, wherein the vector comprises a plasmid.

5. The method of claim 1, wherein the effective amount of the vector is administered to the subject in a single dose.

6. The method of 1, wherein the effective amount of the vector is administered to the subject in a single dose that attenuates re-infection of the subject by RSV.

* * * * *

UNITED STATES PATENT AND TRADEMARK OFFICE

CERTIFICATE OF CORRECTION

PATENT NO. : 9,089,590 B2
APPLICATION NO. : 13/765858
DATED : July 28, 2015
INVENTOR(S) : Shyam S. Mohapatra and Weidong Zhang It is certified that error appears in the above-identified patent and that said Letters Patent is hereby corrected as shown below:

In the Specification

Column 10,
Line 57, "(e.g. RSV" should read --(e.g., RSV--.

Column 11,
Line 38, "phenotype. etc." should read --phenotype, etc.--.

Column 21,
Line 67, "herein." should read --herein,--.

Column 22,
Line 14, "(2002). supra." should read --(2002), supra.--.

Column 24,
Line 28, "*E. coli* lac or tip" should read --*E. coli* lac or trp--.

Signed and Sealed this
Eighth Day of March, 2016

Michelle K. Lee
*Director of the United States Patent and Trademark Office*

SEQUENCE LISTING

```
<160> NUMBER OF SEQ ID NOS: 15

<210> SEQ ID NO 1
<211> LENGTH: 62
<212> TYPE: DNA
<213> ORGANISM: Artificial Sequence
<220> FEATURE:
<223> OTHER INFORMATION: nucleotide sequence of the siRNA for RSV NS1,
      designated siNS1

<400> SEQUENCE: 1

ggcagcaatt cattgagtat gcttctcgaa ataagcatac tcaatgaatt gctgcctttt     60

tg                                                                    62


<210> SEQ ID NO 2
<211> LENGTH: 54
<212> TYPE: DNA
<213> ORGANISM: Artificial Sequence
<220> FEATURE:
<223> OTHER INFORMATION: nucleotide sequence of the siRNA for RSV NS1,
      designated siNS1a

<400> SEQUENCE: 2

gtgtgccctg ataacaatat tcaagagata ttgttatcag ggcacacttt tttg           54


<210> SEQ ID NO 3
<211> LENGTH: 53
<212> TYPE: DNA
<213> ORGANISM: Artificial Sequence
<220> FEATURE:
<223> OTHER INFORMATION: nucleotide sequence of the siRNA for HPV18 E7,
      designated siE7

<400> SEQUENCE: 3

gaaaacgatg aaatagatgt tcaagagaca tctatttcat cgttttcttt ttt            53


<210> SEQ ID NO 4
<211> LENGTH: 63
<212> TYPE: DNA
<213> ORGANISM: Artificial Sequence
<220> FEATURE:
<223> OTHER INFORMATION: nucleotide sequence of the siRNA for type A
      Influenza virus PB2, designated siPB2

<400> SEQUENCE: 4

ggctatattc aatatggaaa gaactcgagt tttgttcttt ccatattgaa tatagccttt     60

ttg                                                                   63


<210> SEQ ID NO 5
<211> LENGTH: 56
<212> TYPE: DNA
<213> ORGANISM: Artificial Sequence
<220> FEATURE:
<223> OTHER INFORMATION: nucleotide sequence of the siRNA for type A
      Influenza virus pUR, designated siUR

<400> SEQUENCE: 5

ggtcacgatc agaatacttc gctcgagcga agtattctga tcgtgaccct tttttg         56


<210> SEQ ID NO 6
<211> LENGTH: 20
<212> TYPE: DNA
<213> ORGANISM: Artificial Sequence
<220> FEATURE:
<223> OTHER INFORMATION: IFN-beta forward primer
```

<400> SEQUENCE: 6
ataagcagct ccagctccaa 20

<210> SEQ ID NO 7
<211> LENGTH: 20
<212> TYPE: DNA
<213> ORGANISM: Artificial Sequence
<220> FEATURE:
<223> OTHER INFORMATION: IFN-beta reverse primer

<400> SEQUENCE: 7
ctgtctgctg gtggagttca 20

<210> SEQ ID NO 8
<211> LENGTH: 20
<212> TYPE: DNA
<213> ORGANISM: Artificial Sequence
<220> FEATURE:
<223> OTHER INFORMATION: RSV-NS1 forward primer

<400> SEQUENCE: 8
atggggtgca attcattgag 20

<210> SEQ ID NO 9
<211> LENGTH: 19
<212> TYPE: DNA
<213> ORGANISM: Artificial Sequence
<220> FEATURE:
<223> OTHER INFORMATION: RSV-NS1 reverse primer

<400> SEQUENCE: 9
cagggcacac ttcactgct 19

<210> SEQ ID NO 10
<211> LENGTH: 20
<212> TYPE: DNA
<213> ORGANISM: Artificial Sequence
<220> FEATURE:
<223> OTHER INFORMATION: RSV-F forward primer

<400> SEQUENCE: 10
tgcagtgcag ttagcaaagg 20

<210> SEQ ID NO 11
<211> LENGTH: 20
<212> TYPE: DNA
<213> ORGANISM: Artificial Sequence
<220> FEATURE:
<223> OTHER INFORMATION: RSV-F reverse primer

<400> SEQUENCE: 11
tctggctcga ttgtttgttg 20

<210> SEQ ID NO 12
<211> LENGTH: 19
<212> TYPE: DNA
<213> ORGANISM: Artificial Sequence
<220> FEATURE:
<223> OTHER INFORMATION: GAPDH forward primer

<400> SEQUENCE: 12
cccttcattg acctcaact 19

<210> SEQ ID NO 13
<211> LENGTH: 17

<212> TYPE: DNA
<213> ORGANISM: Artificial Sequence
<220> FEATURE:
<223> OTHER INFORMATION: GAPDH reverse primer

<400> SEQUENCE: 13
gacgccagtg gactcca 17

<210> SEQ ID NO 14
<211> LENGTH: 15222
<212> TYPE: DNA
<213> ORGANISM: Human respiratory syncytial virus

<400> SEQUENCE: 14
acgcgaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaacgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780
cttgatgaaa aacaggccac atttacattc ctggtcaact atgaaatgaa actattacac 840
aaagtaggaa gcactaaata taaaaaatat actgaataca acacaaaata tggcactttc 900
cctatgccaa tattcatcaa tcatgatggg ttcttagaat gcattggcat taagcctaca 960
aagcatactc ccataatata caagtatgat ctcaatccat aaatttcaac acaatattca 1020
cacaatctaa aacaacaact ctatgcataa ctatactcca tagtccagat ggagcctgaa 1080
aattatagta atttaaaatt aaggagagat ataagataga agatggggca aatacaaaga 1140
tggctcttag caaagtcaag ttgaatgata cactcaacaa agatcaactt ctgtcatcca 1200
gcaaatacac catccaacgg agcacaggag atagtattga tactcctaat tatgatgtgc 1260
agaaacacat caataagtta tgtggcatgt tattaatcac agaagatgct aatcataaat 1320
tcactgggtt aataggtatg ttatatgcga tgtctaggtt aggaagagaa gacaccataa 1380
aaatactcag agatgcggga tatcatgtaa aagcaaatgg agtagatgta acaacacatc 1440
gtcaagacat taatggaaaa gaaatgaaat ttgaagtgtt aacattggca agcttaacaa 1500
ctgaaattca aatcaacatt gagatagaat ctagaaaatc ctacaaaaaa atgctaaaag 1560
aaatgggaga ggtagctcca gaatacaggc atgactctcc tgattgtggg atgataatat 1620
tatgtatagc agcattagta ataactaaat tagcagcagg ggacagatct ggtcttacag 1680
ccgtgattag gagagctaat aatgtcctaa aaaatgaaat gaaacgttac aaaggcttac 1740
tacccaagga catagccaac agcttctatg aagtgtttga aaaacatccc cactttatag 1800
atgtttttgt tcattttggt atagcacaat cttctaccag aggtggcagt agagttgaag 1860

-continued

```
ggatttttgc aggattgttt atgaatgcct atggtgcagg gcaagtgatg ttacggtggg   1920
gagtcttagc aaaatcagtt aaaaatatta tgttaggaca tgctagtgtg caagcagaaa   1980
tggaacaagt tgttgaggtt tatgaatatg cccaaaaatt gggtggtgaa gcaggattct   2040
accatatatt gaacaaccca aaagcatcat tattatcttt gactcaattt cctcacttct   2100
ccagtgtagt attaggcaat gctgctggcc taggcataat gggagagtac agaggtacac   2160
cgaggaatca agatctatat gatgcagcaa aggcatatgc tgaacaactc aaagaaaatg   2220
gtgtgattaa ctacagtgta ctagacttga cagcagaaga actagaggct atcaaacatc   2280
agcttaatcc aaaagataat gatgtagagc tttgagttaa taaaaaatgg ggcaaataaa   2340
tcatcatgga aaagtttgct cctgaattcc atggagaaga tgcaaacaac agggctacta   2400
aattcctaga atcaataaag ggcaaattca catcacccaa agatcccaag aaaaaagata   2460
gtatcatatc tgtcaactca atagatatag aagtaaccaa agaaagccct ataacatcaa   2520
attcaactat tatcaaccca acaaatgaga cagatgatac tgcagggaac aagcccaatt   2580
atcaaagaaa acctctagta agtttcaaag aagaccctac accaagtgat aatccctttt   2640
ctaaactata caaagaaacc atagaaacat ttgataacaa tgaagaagaa tccagctatt   2700
catacgaaga aataaatgat cagacaaacg ataatataac agcaagatta gataggattg   2760
atgaaaaatt aagtgaaata ctaggaatgc ttcacacatt agtagtggca agtgcaggac   2820
ctacatctgc tcgggatggt ataagagatg ccatgattgg tttaagagaa gaaatgatag   2880
aaaaaatcag aactgaagca ttaatgacca atgacagatt agaagctatg gcaagactca   2940
ggaatgagga aagtgaaaag atggcaaaag acacatcaga tgaagtgtct ctcaatccaa   3000
catcagagaa attgaacaac ctattggaag ggaatgatag tgacaatgat ctatcacttg   3060
aagatttctg attagttacc actcttcaca tcaacacaca ataccaacag aagaccaaca   3120
aactaaccaa cccaatcatc caaccaaaca tccatccgcc aatcagccaa acagccaaca   3180
aaacaaccag ccaatccaaa actaaccacc cggaaaaaat ctataatata gttacaaaaa   3240
aaggaaaggg tggggcaaat atggaaacat acgtgaacaa gcttcacgaa ggctccacat   3300
acacagctgc tgttcaatac aatgtcttag aaaaagacga tgaccctgca tcacttacaa   3360
tatgggtgcc catgttccaa tcatctatgc cagcagattt acttataaaa gaactagcta   3420
atgtcaacat actagtgaaa caaatatcca cacccaaggg accttcacta agagtcatga   3480
taaactcaag aagtgcagtg ctagcacaaa tgcccagcaa atttaccata tgcgctaatg   3540
tgtccttgga tgaaagaagc aaactagcat atgatgtaac cacaccctgt gaaatcaagg   3600
catgtagtct aacatgccta aaatcaaaaa atatgttgac tacagttaaa gatctcacta   3660
tgaagacact caaccctaca catgatatta ttgctttatg tgaatttgaa aacatagtaa   3720
catcaaaaaa agtcataata ccaacatacc taagatccat cagtgtcaga aataaagatc   3780
tgaacacact tgaaaatata acaaccactg aattcaaaaa tgctatcaca aatgcaaaaa   3840
tcatccctta ctcaggatta ctattagtca tcacagtgac tgacaacaaa ggagcattca   3900
aatacataaa gccacaaagt caattcatag tagatcttgg agcttaccta gaaaaagaaa   3960
gtatatatta tgttaccaca aattggaagc acacagctac acgatttgca atcaaaccca   4020
tggaagatta accttttttcc tctacatcag tgtgttaatt catacaaact ttctacctac   4080
attcttcact tcaccatcac aatcacaaac actctgtggt tcaaccaatc aaacaaaact   4140
tatctgaagt cccagatcat cccaagtcat tgtttatcag atctagtact caaataagtt   4200
aataaaaaat atacacatgg ggcaaataat cattggagga aatccaacta atcacaatat   4260
```

```
ctgttaacat agacaagtcc acacaccata cagaatcaac caatggaaaa tacatccata   4320
acaatagaat tctcaagcaa attctggcct tactttacac taatacacat gatcacaaca   4380
ataatctctt tgctaatcat aatctccatc atgattgcaa tactaaacaa actttgtgaa   4440
tataacgtat tccataacaa aacctttgag ttaccaagag ctcgagtcaa cacatagcat   4500
tcatcaatcc aacagcccaa aacagtaacc ttgcatttaa aaatgaacaa cccctacctc   4560
tttacaacac ctcattaaca tcccaccatg caaaccacta tccatactat aaagtagtta   4620
attaaaaata gtcataacaa tgaactagga tatcaagact aacaataaca ttggggcaaa   4680
tgcaaacatg tccaaaaaca aggaccaacg caccgctaag acattagaaa ggacctggga   4740
cactctcaat catttattat tcatatcatc gtgcttatat aagttaaatc ttaaatctgt   4800
agcacaaatc acattatcca ttctggcaat gataatctca acttcactta taattgcagc   4860
catcatattc atagcctcgg caaaccacaa agtcacacca acaactgcaa tcatacaaga   4920
tgcaacaagc cagatcaaga acacaacccc aacatacctc acccagaatc ctcagcttgg   4980
aatcagtccc tctaatccgt ctgaaattac atcacaaatc accaccatac tagcttcaac   5040
aacaccagga gtcaagtcaa ccctgcaatc cacaacagtc aagaccaaaa acacaacaac   5100
aactcaaaca caacccagca agcccaccac aaaacaacgc caaaacaaac caccaagcaa   5160
acccaataat gattttcact ttgaagtgtt caactttgta ccctgcagca tatgcagcaa   5220
caatccaacc tgctgggcta tctgcaaaag aataccaaac aaaaaaccag gaaagaaaac   5280
cactaccaag cccacaaaaa aaccaaccct caagacaacc aaaaaagatc ccaaacctca   5340
aaccactaaa tcaaaggaag tacccaccac caagcccaca gaagagccaa ccatcaacac   5400
caccaaaaca aacatcataa ctacactact cacctccaac accacaggaa atccagaact   5460
cacaagtcaa atggaaacct tccactcaac ttcctccgaa ggcaatccaa gcccttctca   5520
agtctctaca acatccgagt acccatcaca accttcatct ccacccaaca caccacgcca   5580
gtagttactt aaaaacatat tatcacaaaa agccatgacc aacttaaaca gaatcaaaat   5640
aaactctggg gcaaataaca atggagttgc taatcctcaa agcaaatgca attaccacaa   5700
tcctcactgc agtcacattt tgttttgctt ctggtcaaaa catcactgaa gaattttatc   5760
aatcaacatg cagtgcagtt agcaaaggct atcttagtgc tctgagaact ggttggtata   5820
ccagtgttat aactatagaa ttaagtaata tcaaggaaaa taagtgtaat ggaacagatg   5880
ctaaggtaaa attgataaaa caagaattag ataaatataa aaatgctgta acagaattgc   5940
agttgctcat gcaaagcaca ccaccaacaa acaatcgagc cagaagagaa ctaccaaggt   6000
ttatgaatta tacactcaac aatgccaaaa aaaccaatgt aacattaagc aagaaaagga   6060
aaagaagatt tcttgttttt ttgttaggtg ttggatctgc aatcgccagt ggcgttgctg   6120
tatctaaggt cctgcaccta gaaggggaag tgaacaagat caaaagtgct ctactatcca   6180
caaacaaggc tctagtcagc ttatcaaatg gagttagtgt cttaaccagc aaagtgttag   6240
acctcaaaaa ctatatagat aaacaattgt tacctattgt gaacaagcaa agctgcagca   6300
tatcaaatat agaaactgtg atagagttcc aacaaaagaa caacagacta ctagagatta   6360
ccagggaatt tagtgttaat gcaggtgtaa ctacacctgt aagcacttac atgttaacta   6420
atagtgaatt attgtcatta atcaatgata tgcctataac aaatgatcag aaaaagttaa   6480
tgtccaacaa tgttcaaata gttagacagc aaagttactc tatcatgtcc ataataaaag   6540
aggaagtctt agcatatgta gtacaattac cactatatgg tgttatagat acaccctgtt   6600
```

-continued

```
ggaaactaca cacatcccct ctatgtacaa ccaacacaaa agaagggtcc aacatctgtt   6660
taacaagaac tgacagagga tggtactgtg acaatgcagg atcagtatct ttcttcccac   6720
aagctgaaac atgtaaagtt caatcaaatc gagtattttg tgacacaatg aacagtttaa   6780
cattaccaag tgaaataaat ctctgcaatg ttgacatatt caaccccaaa tatgattgta   6840
aaattatgac ttcaaaaaca gatgtaagca gctccgttat cacatctcta ggagccattg   6900
tgtcatgcta tggcaaaact aaatgtacag catccaataa aaatcgtgga atcataaaga   6960
cattttctaa cgggtgcgat tatgtatcaa ataaagggat ggacactgtg tctgtaggta   7020
acacattata ttatgtaaat aagcaagaag gtaaaagtct ctatgtaaaa ggtgaaccaa   7080
taataaattt ctatgaccca ttagtattcc cctctgatga atttgatgca tcaatatctc   7140
aagtcaacga gaagattaac cagagcctag catttattcg taaatccgat gaattattac   7200
ataatgtaaa tgctggtaaa tccaccacaa atatcatgat aactactata attatagtga   7260
ttatagtaat attgttatca ttaattgctg ttggactgct cttatactgt aaggccagaa   7320
gcacaccagt cacactaagc aaagatcaac tgagtggtat aaataatatt gcatttagta   7380
actaaataaa aatagcacct aatcatgttc ttacaatggt ttactatctg ctcatagaca   7440
acccatctgt cattggattt tcttaaaatc tgaacttcat cgaaactctc atctataaac   7500
catctcactt acactattta agtagattcc tagtttatag ttatataaaa cacaattgaa   7560
tgccagatta acttaccatc tgtaaaaatg aaaactgggg caaatatgtc acgaaggaat   7620
ccttgcaaat ttgaaattcg aggtcattgc ttaaatggta agaggtgtca ttttagtcat   7680
aattattttg aatggccacc ccatgcactg cttgtaagac aaaactttat gttaaacaga   7740
atacttaagt ctatggataa aagtatagat accttatcag aaataagtgg agctgcagag   7800
ttggacagaa cagaagagta tgctcttggt gtagttggag tgctagagag ttatatagga   7860
tcaataaaca atataactaa acaatcagca tgtgttgcca tgagcaaact cctcactgaa   7920
ctcaatagtg atgatatcaa aaagctgagg gacaatgaag agctaaattc acccaagata   7980
agagtgtaca atactgtcat atcatatatt gaaagcaaca ggaaaaacaa taaacaaact   8040
atccatctgt taaaaagatt gccagcagac gtattgaaga aaaccatcaa aaacacattg   8100
gatatccata agagcataac catcaacaac ccaaaagaat caactgttag tgatacaaat   8160
gaccatgcca aaaataatga tactacctga caaatatcct tgtagtataa cttccatact   8220
aataacaagt agatgtagag ttactatgta taatcaaaag aacacactat atttcaatca   8280
aaacaaccca aataaccata tgtactcacc gaatcaaaca ttcaatgaaa tccattggac   8340
ctctcaagaa ttgattgaca caattcaaat ttttctacaa catctaggta ttattgagga   8400
tatatataca atatatatat tagtgtcata acactcaatt ctaacactca ccacatcgtt   8460
acattattaa ttcaaacaat tcaagttgtg ggacaaaatg gatcccatta ttaatggaaa   8520
ttctgctaat gtttatctaa ccgatagtta tttaaaaggt gttatctctt tctcagagtg   8580
taatgcttta ggaagttaca tattcaatgg tccttatctc aaaaatgatt ataccaactt   8640
aattagtaga caaaatccat taatagaaca catgaatcta aagaaactaa atataacaca   8700
gtccttaata tctaagtatc ataaaggtga aataaaatta gaagaaccta cttattttca   8760
gtcattactt atgacataca agagtatgac ctcgtcagaa cagattgcta ccactaattt   8820
acttaaaaag ataataagaa gagctataga aataagtgat gtcaaagtct atgctatatt   8880
gaataaacta gggcttaaag aaaaggacaa gattaaatcc aacaatggac aagatgaaga   8940
caactcagtt attacgacca taatcaaaga tgatatactt tcagctgtta aagataatca   9000
```

```
atctcatctt aaagcagaca aaaatcactc tacaaaacaa aaagacacaa tcaaaacaac   9060
actcttgaag aaattgatgt gttcaatgca acatcctcca tcatggttaa tacattggtt   9120
taacttatac acaaaattaa acaacatatt aacacagtat cgatcaaatg aggtaaaaaa   9180
ccatgggttt acattgatag ataatcaaac tcttagtgga tttcaattta ttttgaacca   9240
atatggttgt atagtttatc ataaggaact caaaagaatt actgtgacaa cctataatca   9300
attcttgaca tggaaagata ttagccttag tagattaaat gtttgtttaa ttacatggat   9360
tagtaactgc ttgaacacat taaataaaag cttaggctta agatgcggat tcaataatgt   9420
tatcttgaca caactattcc tttatggaga ttgtatacta aagctatttc acaatgaggg   9480
gttctacata ataaaagagg tagagggatt tattatgtct ctaattttaa atataacaga   9540
agaagatcaa ttcagaaaac gattttataa tagtatgctc aacaacatca cagatgctgc   9600
taataaagct cagaaaaatc tgctatcaag agtatgtcat acattattag ataagacagt   9660
gtccgataat ataataaatg gcagatggat aattctatta agtaagttcc ttaaattaat   9720
taagcttgca ggtgacaata accttaacaa tctgagtgaa ctatattttt tgttcagaat   9780
atttggacac ccaatggtag atgaaagaca agccatggat gctgttaaaa ttaattgcaa   9840
tgagaccaaa ttttacttgt taagcagtct gagtatgtta agaggtgcct ttatatatag   9900
aattataaaa gggtttgtaa ataattacaa cagatggcct actttaagaa atgctattgt   9960
ttaccctta agatggttaa cttactataa actaaacact tatccttctt tgttggaact  10020
tacagaaaga gatttgattg tgttatcagg actacgtttc tatcgtgagt ttcggttgcc  10080
taaaaaagtg gatcttgaaa tgattataaa tgataaagct atatcacctc ctaaaaattt  10140
gatatggact agtttcccta gaaattacat gccatcacac atacaaaact atatagaaca  10200
tgaaaaatta aaattttccg agagtgataa atcaagaaga gtattagagt attatttaag  10260
agataacaaa ttcaatgaat gtgatttata caactgtgta gttaatcaaa gttatctcaa  10320
caaccctaat catgtggtat cattgacagg caaagaaaga gaactcagtg taggtagaat  10380
gtttgcaatg caaccgggaa tgttcagaca ggttcaaata ttggcagaga aaatgatagc  10440
tgaaaacatt ttacaattct ttcctgaaag tcttacaaga tatggtgatc tagaactaca  10500
aaaaatatta gaattgaaag caggaataag taacaaatca aatcgctaca atgataatta  10560
caacaattac attagtaagt gctctatcat cacagatctc agcaaattca atcaagcatt  10620
tcgatatgaa acgtcatgta tttgtagtga tgtgctggat gaactgcatg gtgtacaatc  10680
tctattttcc tggttacatt taactattcc tcatgtcaca ataaatatgca catataggca  10740
tgcacccccc tatataggag atcatattgt agatcttaac aatgtagatg aacaaagtgg  10800
attatataga tatcacatgg gtggcatcga agggtggtgt caaaaactgt ggaccataga  10860
agctatatca ctattggatc taatatctct caaagggaaa ttctcaatta ctgctttaat  10920
taatggtgac aatcaatcaa tagatataag caaaccaatc agactcatgg aaggtcaaac  10980
tcatgctcaa gcagattatt tgctagcatt aaatagcctt aaattactgt ataaagagta  11040
tgcaggcata ggccacaaat taaaaggaac tgagacttat atatcacgag atatgcaatt  11100
tatgagtaaa acaattcaac ataacggtgt atattaccca gctagtataa agaaagtcct  11160
aagagtggga ccgtggataa acactatact tgatgatttc aaagtgagtc tagaatctat  11220
aggtagtttg acacaagaat tagaatatag aggtgaaagt ctattatgca gtttaatatt  11280
tagaaatgta tggttatata atcagattgc tctacaatta aaaaatcatg cattatgtaa  11340
```

-continued

```
caataaacta tatttggaca tattaaaggt tctgaaacac ttaaaaacct tttttaatct  11400
tgataatatt gatacagcat taacattgta tatgaattta cccatgttat ttggtggtgg  11460
tgatcccaac ttgttatatc gaagtttcta tagaagaact cctgacttcc tcacagaggc  11520
tatagttcac tctgtgttca tacttagtta ttatacaaac catgacttaa aagataaact  11580
tcaagatctg tcagatgata gattgaataa gttcttaaca tgcataatca cgtttgacaa  11640
aaaccctaat gctgaattcg taacattgat gagagatcct caagctttag ggtctgagag  11700
acaagctaaa attactagcg aaatcaatag actggcagtt acagaggttt tgagtacagc  11760
tccaaacaaa atattctcca aaagtgcaca acattatact actacagaga tagatctaaa  11820
tgatattatg caaaatatag aacctacata tcctcatggg ctaagagttg tttatgaaag  11880
tttacccttt tataaagcag agaaaatagt aaatcttata tcaggtacaa aatctataac  11940
taacatactg gaaaaaactt ctgccataga cttaacagat attgatagag ccactgagat  12000
gatgaggaaa aacataactt tgcttataag gatacttcca ttggattgta acagagataa  12060
aagagagata ttgagtatgg aaaacctaag tattactgaa ttaagcaaat atgttaggga  12120
aagatcttgg tctttatcca atatagttgg tgttacatca cccagtatca tgtatacaat  12180
ggacatcaaa tatactacaa gcactatatc tagtggcata attatagaga aatataatgt  12240
taacagttta acacgtggtg agagaggacc cactaaacca tgggttggtt catctacaca  12300
agagaaaaaa acaatgccag tttataatag acaagtctta accaaaaaac agagagatca  12360
aatagatcta ttagcaaaat tggattgggt gtatgcatct atagataaca aggatgaatt  12420
catggaagaa ctcagcatag gaacccttgg gttaacatat gaaaaggcca agaaattatt  12480
tccacaatat ttaagtgtca attatttgca tcgccttaca gtcagtagta gaccatgtga  12540
attccctgca tcaataccag cttatagaac aacaaattat cactttgaca ctagccctat  12600
taatcgcata ttaacagaaa agtatggtga tgaagatatt gacatagtat tccaaaactg  12660
tataagcttt ggccttagtt taatgtcagt agtagaacaa tttactaatg tatgtcctaa  12720
cagaattatt ctcataccta agcttaatga gatacatttg atgaaacctc ccatattcac  12780
aggtgatgtt gatattcaca agttaaaaca agtgatacaa aaacagcata tgtttttacc  12840
agacaaaata agtttgactc aatatgtgga attattctta agtaataaaa cactcaaatc  12900
tggatctcat gttaattcta atttaatatt ggcacataaa atatctgact attttcataa  12960
tacttacatt ttaagtacta atttagctgg acattggatt ctgattatac aacttatgaa  13020
agattctaaa ggtatttttg aaaaagattg ggagaggga tatataactg atcatatgtt  13080
tattaatttg aaagttttct tcaatgctta taagacctat ctcttgtgtt ttcataaagg  13140
ttatggcaaa gcaaagctgg agtgtgatat gaacacttca gatcttctat gtgtattgga  13200
attaatagac agtagttatt ggaagtctat gtctaaggta tttttagaac aaaaagttat  13260
caaatacatt cttagccaag atgcaagttt acatagagta aaaggatgtc atagcttcaa  13320
attatggttt cttaaacgtc ttaatgtagc agaattcaca gtttgccctt gggttgttaa  13380
catagattat catccaacac atatgaaagc aatattaact tatatagatc ttgttagaat  13440
gggattgata aatatagata gaatacacat taaaaataaa cacaaattca atgatgaatt  13500
ttatacttct aatctcttct acattaatta taacttctca gataatactc atctattaac  13560
taaacatata aggattgcta attctgaatt agaaaataat tacaacaaat tatatcatcc  13620
tacaccagaa accctagaga atatactagc caatccgatt aaaagtaatg acaaaaagac  13680
actgaatgac tattgtatag gtaaaaatgt tgactcaata atgttaccat tgttatctaa  13740
```

```
taagaagctt attaaatcgt ctgcaatgat tagaaccaat tacagcaaac aagatttgta  13800
taatttattc cctatggttg tgattgatag aattatagat cattcaggca atacagccaa  13860
atccaaccaa ctttacacta ctacttccca ccaaatatct ttagtgcaca atagcacatc  13920
actttactgc atgcttcctt ggcatcatat taatagattc aattttgtat ttagttctac  13980
aggttgtaaa attagtatag agtatatttt aaaagatctt aaaattaaag atcccaattg  14040
tatagcattc ataggtgaag gagcagggaa tttattattg cgtacagtag tggaacttca  14100
tcctgacata agatatattt acagaagtct gaaagattgc aatgatcata gtttacctat  14160
tgagttttta aggctgtaca atggacatat caacattgat tatggtgaaa atttgaccat  14220
tcctgctaca gatgcaacca acaacattca ttggtcttat ttacatataa agtttgctga  14280
acctatcagt ctttttgtct gtgatgccga attgtctgta acagtcaact ggagtaaaat  14340
tataatagaa tggagcaagc atgtaagaaa gtgcaagtac tgttcctcag ttaataaatg  14400
tatgttaata gtaaaatatc atgctcaaga tgatattgat ttcaaattag acaatataac  14460
tatattaaaa acttatgtat gcttaggcag taagttaaag ggatcggagg tttacttagt  14520
ccttacaata ggtcctgcga atatattccc agtatttaat gtagtacaaa atgctaaatt  14580
gatactatca agaaccaaaa atttcatcat gcctaagaaa gctgataaag agtctattga  14640
tgcaaatatt aaaagtttga taccctttct ttgttaccct ataacaaaaa aaggaattaa  14700
tactgcattg tcaaaactaa agagtgttgt tagtggagat atactatcat attctatagc  14760
tggacgtaat gaagttttca gcaataaact tataaatcat aagcatatga acatcttaaa  14820
atggttcaat catgttttaa atttcagatc aacagaacta aactataacc atttatatat  14880
ggtagaatct acatatcctt acctaagtga attgttaaac agcttgacaa ccaatgaact  14940
taaaaaactg attaaaatca caggtagtct gttatacaac tttcataatg aataatgaat  15000
aaagatctta taataaaaat tcccatagct atacactaac actgtattca attatagtta  15060
ttaaaaatta aaaatcatat aattttttaa ataactttta gtgaactaat cctaaagtta  15120
tcattttaat cttggaggaa taaatttaaa ccctaatcta attggtttat atgtgtatta  15180
actaaattac gagatattag tttttgacac tttttttctc gt                      15222
```

<210> SEQ ID NO 15
<211> LENGTH: 15140
<212> TYPE: DNA
<213> ORGANISM: Bovine respiratory syncytial virus

<400> SEQUENCE: 15

```
acgcgaaaaa atgcgtataa caaacctgta catccaaaaa agatcggggc aaataaaacc     60
ttgaaaggga gttttcccct ctcttctttc tacagaaaat gggcagtgaa acattgagtg    120
taattcaagt cagattaagg aatatatatg ataatgataa agtagcattg cttaaaataa    180
catgtcatac caatagatta atacttctaa ctcacacatt ggccaaatca gtcatacata    240
caattaaatt aagtggtata gtattcatac atattataac cagtagtgat tactgtccta    300
catctgatat tatcaatagt gccaatttca cttcaatgcc tatattacaa aatggaggat    360
atatatggga attgatggag ttaacacatt gtttccaaac aaacggttta atagatgata    420
attgtgaaat aacattttct aaaaggttaa gtgattcaga attagctaaa tattcaaatc    480
aattatctac tcttcttggt ctgaattaga gccctaaatc aatagccaac accagatgga    540
ctaagctaac taaatgtaat agtttataaa aattaattgg ggcaaataaa tcagttcccc    600
```

-continued

```
aaccagccat gagcacccca aatcccgaaa ccactgctca gagattgata gtaaatgata    660
tgaggccatt atcaatagaa acagaaataa tatctttgac caaagatatt attacacata    720
cattcatata tctaataaac catgagtgta tagtacgcaa actcgatgaa cgacaggcca    780
catttacatt ccttgtcaat tatgaaatga agctattgca taaagtgggt agcacaaaat    840
acaataaata cacagaatac aacagaaaat atggtacatt tccaatgcct atatttatca    900
accatgatgg ttttttagag tgtataggta tcaagcctac aagaaatact cctataaatat    960
ataagtatga tttaaatcca taggcacttt tcaaaattta attcacacag tgttatcttt   1020
tggtaccaat gtcaaccaaa ttcccacata gtgcatagta gtaattaaaa aagaaccagg   1080
ttagaaacaa aaaaaggtag agaataacaa caaacaaaaa tgaaatgtgg ggcaaataca   1140
aaaatggctc ttagcaaggt caaactaaat gacactttca acaaggatca actgttgtca   1200
accagcaaat atactattca acgtagtaca ggtgacaaca ttgatatacc caattacgat   1260
gtgcaaaaac atctcaataa gttgtgtggt atgctattaa taacagaaga tgccaatcat   1320
aaatttacag gactgatagg tatgttatat gctatgtccc gattggggag agaagatacc   1380
cttaaaatac tcaaagatgc aggctaccaa gtgagggcca atggggttga tgtgataaca   1440
catcgacagg atgtgaatgg aaaagaaatg aaatttgaag tgctaacatt agtcagctta   1500
acatcagaag ttcaaggtaa tatagaaata gagtcaagga agtcttacaa aaagatgcta   1560
aaagagatgg gagaggtagc tccagaatac agacatgact ctcctgattg tggtatgata   1620
gtgctatgtg ttgctgcttt ggttataaca aaattagcag caggtgatag gtcaggcctc   1680
actgcagtca ttaggagagc caacaatgta ctaaggaatg aaatgaaacg atacaaagga   1740
ctcatcccga aagatatagc caacagcttc tatgaagtat ttgaaaagta ccctcattac   1800
atagatgtat tcgtacattt tggcattgct caatcctcaa ctagaggagg tagtagggta   1860
gaaggaatct ttgcagggtt attcatgaat gcatatggag caggtcaagt gatgttaaga   1920
tggggtgtac tagccaaatc agtcaagaat attatgcttg gtcatgccag cgtacaagca   1980
gaaatggaac aggttgtaga agtctatgaa tatgcacaaa agttaggtgg agaagctggt   2040
ttttatcaca tactgaacaa ccctaaagca tcattgttat ccttaacaca attccccaat   2100
ttctctagtg tagtcctagg caatgctgca ggactaggta taatgggtga gtatagaggt   2160
acaccaagaa accaagactt gtatgatgct gccaaagcat atgcagaaca actaaaagag   2220
aatggggtca tcaattacag tgtattggat ctgactacag aggaattaga ggcaatcaag   2280
aaccaattga atcccaaaga taatgatgtg gaattgtgag ttaataaaaa catggggcaa   2340
atacgtcagt atggaaaaat ttgcacctga gtttcatgga gaagatgcca atacaaaagc   2400
aaccaagttt cttgaatccc taaaagggaa atttacttct tctaaggatt ctaggaaaaa   2460
agatagtata atatcagtta attccgtaga catagaatta cctaaagaga gtcctataac   2520
atctaccaat caaaatatca accaaccaag tgagatcaat gacactattg ctacaaatca   2580
agttcatata agaaagcctt tggtaagctt caaagaagaa ctgccatcaa gtgaaaaccc   2640
ctttacaagg ctgtataagg aaactataga aacatttgac aataatgaag aagaatcaag   2700
ctactcatat gatgagataa atgatcaaac aaatgataat ataacagcaa gactagatag   2760
gatagatgaa aaattaagcg agataatagg aatgctccat acattagttg tggctagtgc   2820
aggaccaaca gctgctcgtg acggtataag agatgccatg gtagggctcc gagaagagat   2880
gattgagaaa ataagatcag aagctttaat gaccaacgat aggttagaag caatggccag   2940
gcttagggat gaagaaagtg aaaagatgac aaaagataca tcagatgaag taaaattaac   3000
```

```
ccctacctca gagaagctga acatggtatt agaagatgaa agtagtgaca atgatctatc   3060
acttgaagat ttctgaatag caaccagccc acccactaac agattagtca gatagatcaa   3120
ccatcaatga taaagccacc taatcaacca gccaaccagt cactcaacca gcctgtgatt   3180
ccacatagtt agtaaaaata aagtaaaatt ggggcaaata tggagacata cgtgaacaaa   3240
ctccatgaag gatcaactta cacagctgct gttcagtaca atgtcataga aaaagatgat   3300
gatcctgcat ctctcacaat atgggttcct atgttccaat catccatctc tgctgatttg   3360
cttataaaag aactaatcaa tgtgaacata ttagttcgac aaatttctac tctgaaaggt   3420
ccttcattga agattatgat aaactcaaga agtgctgtac tagcccaaat gcccagcaaa   3480
tttaccataa gtgcaaatgt atcattggat gaacgaagca aattagcata tgacataact   3540
actccttgtg aaattaaggc ttgtagttta acatgtttaa aggtgaaaaa tatgctcaca   3600
actgtgaaag atctcaccat gaaaacattc aatcctaccc atgagatcat tgcactgtgt   3660
gaatttgaaa atatcatgac atccaaaaga gttgttatac caactttctt aaggtcaatc   3720
aatgtaaaag caaaggattt ggactcacta gagaatatag ctaccacaga gttcaaaaat   3780
gccatcacta atgctaaaat tataccttat gctgggttgg tattagttat cactgtaact   3840
gacaataaag gggcattcaa gtacattaaa ccacaaagtc aatttatagt agatcttggt   3900
gcatatctag agaaagagag catatattat gtaactacaa attggaaaca cacggccact   3960
aaattctcca ttaagcctat agaggactga ttctcacaca acttatctta acacaacaga   4020
agactccctt aataacttac taatcatcat tgtaatcgaa tcttatttgc tgctctatca   4080
accataatca tcatattttc tcaacctgat taacccttca attcatcttg tagattatac   4140
ctcagttaga taaataaaaa ttatgaatgc caacaaagat tatgtggggc aaataaaatc   4200
tgcatccaat caagtacagc atacaccaga aactcctcga atccaccagc tggttgaact   4260
tattacaatg aacaatacat ctaccataat agagtttact ggtgaatttt ggacttactt   4320
tacattagcc tttatgatgt taaccatagg tttttctttt attgtcacat cattagtggc   4380
agcaatactg aacaaattat gtgacttcaa cgatcatcat acaaatagtc tagacatcag   4440
aactaggctt agaaatgata cacaattgat aacaagagca catgaaggat ccatcaacca   4500
atcaagcaac taagaggaca acaaaacaaa agaaaatagc aacatgcatc aaagttaagc   4560
aaaggaaaac cacaaagaat cagacaatca tcactcatat ctttttagtc tacaaatgct   4620
gcattatgta ctgttaatta gttatttaaa attaaactta aaaatggttt atggttacat   4680
acagatgttg ggcaaatac aagtatgtcc aaccataccc accatcttaa attcaagaca   4740
ttaaagaggg cttggaaagc ctcaaaatac ttcatagtag gattatcatg tttatataag   4800
ttcaatttaa aatcccttgt ccaaacggct ttgaccacct tagcaatgat aaccttgaca   4860
tcactcgtca taacagccat tatttacatt agtgtgggaa atgctaaagc caagcccaca   4920
tccaaaccaa ccatccaaca aacacaacag ccccaaaacc atacctcacc atttttcaca   4980
gagcacaact acaaatcaac tcacacatca attcaaagca ccacactgtc ccaactacca   5040
aacacagaca ccactagaga aactacatac agtcactcaa tcaacgaaac ccaaaacaga   5100
aaaatcaaaa gccaatccac tctacccgcc accagaaaac caccaattaa cccatcggga   5160
agcaaccccc ctgaaaacca ccaagaccac aacaactccc aaacactccc ctatgtgcct   5220
tgcagtacat gtgaaggtaa tcttgcttgt ttatcactct gccaaatcgg gccggagaga   5280
gcaccaagca gagcccctac aatcaccctc aaaaagactc caaaacccaa aaccaccaaa   5340
```

```
aagccaacca agacaacaat ccaccacaga accagccctg aagccaaact gcaacccaaa   5400
aacaacacgg cagctccaca acaaggcatc ctctcttcac cagaacacca cacaaatcaa   5460
tcaactacac agatctaaca acacacctcc atataatatc aattatgttc atatatagtt   5520
atttaaaaag atatgtataa ttcactaatt aaaactgggg caaataagga tggcgacaac   5580
agccatgagg atgatcatca gcattatctt catctctacc tatgtgacac atatcacttt   5640
atgccaaaac ataacagaag aattttatca atcaacatgc agtgcagtta gtagaggtta   5700
ccttagtgca ttaagaactg gatggtatac aagtgtggta acaatagagt tgagcaaaat   5760
acaaaaaaat gtgtgtaaaa gtactgattc aaaagtgaaa ttaataaagc aagaactaga   5820
aagatacaac aatgcagtag tggaattgca gtcacttatg caaaatgaac cggcctcctt   5880
cagtagagca aaaagaggga taccagagtt gatacattat acaagaaact ctacaaaaaa   5940
gttttatggg ctaatgggca agaagagaaa aaggagattt ttaggattct tgctaggtat   6000
tggatctgct gttgcaagtg gtgtagcagt gtccaaagta ctacacctgg agggagaggt   6060
gaataaaatt aaaaatgcac tgctatccac aaataaagca gtagttagtc tatccaatgg   6120
agttagtgtc cttactagca aagtacttga tctaaagaac tatatagaca aagagcttct   6180
acctcaagtt aacaatcatg attgtaggat atccaacata gaaactgtga tagaattcca   6240
acaaaaaaac aatagattgt tagaaattgc tagggaattt agtgtaaatg ctggtattac   6300
cacacctctc agtacataca tgttgaccaa tagtgaatta ctatcactaa ttaatgatat   6360
gcctataacg aatgaccaaa aaaagctaat gtcaagtaat gttcaaatag tcaggcaaca   6420
gagttattcc attatgtcag tggtcaaaga agaagtcata gcttatgttg tacaattgcc   6480
tatttatgga gttatagaca ccccctgttg gaaactacac acctctccgt tatgcaccac   6540
tgataataaa gaagggtcaa acatctgctt aactaggaca gatcgtgggt ggtattgtga   6600
caatgcaggc tctgtgtctt ttttcccaca gacagagaca tgtaaggtac aatcaaatag   6660
agtgttctgt gacacaatga acagtttaac tctgcctact gacgttaact tatgcaacac   6720
tgacatattc aatacaaagt atgactgtaa aataatgaca tctaaaactg acataagtag   6780
ctctgtgata acttcaattg gagctattgt atcatgctat gggaagacaa aatgtacagc   6840
ttctaataaa aatcgtggaa tcataaagac tttttccaat gggtgtgatt atgtatcaaa   6900
caaaggagta gatactgtat ctgttggtaa cacactatat tatgtaaata agctagaggg   6960
gaaagcactc tatataaagg gtgaaccaat tattaattac tatgatccac tagtgtttcc   7020
ttctgatgag tttgatgcat caattgccca agtaaacgca aaaataaacc aaagcctggc   7080
cttcatacgt cgatctgatg agttacttca cagtgtagat gtaggaaaat ccaccacaaa   7140
tgtagtaatt actactatta tcatagtgat agttgtagtg atattaatgt taatagctgt   7200
aggattactg ttttactgta agaccaagag tactcctatc atgttaggga aggatcagct   7260
cagtggtatc aacaatcttt cctttagtaa atgaaatgca taatgtttac aatctaaacc   7320
tcagaatcat aaatgtgatg agctaaattt actaatacat tcaaaagttc tatccgccaa   7380
gacctgcatt tttatcaggt cttacataag ctaaccttac atgctacact caactccatg   7440
ttgatagtta tataaaaata ttatattagt ctcaaagaat aaaattattt aacaaccaat   7500
cattcaaaaa gatggggcaa atatgtcacg aagaaatccc tgcaaatatg agattagggg   7560
acattgctta aatggtaaaa aatgtcattt tagtcataat tactttgaat ggcctccaca   7620
tgctttatta gtgaggcaaa attttatgct aaataagata ttaaaatcta tggacaggaa   7680
caacgatacc ctgtcagaaa taagtggtgc agcagagttg gatagaacag aagaatatgc   7740
```

```
attgggtgta ataggagttt tggaaagtta cctaggctct atcaataata taacaaaaca   7800
atcagcctgt gttgctatga gtaaactatt agccgagatt aacaatgatg acataaagag   7860
attgaggaac aaggaagtgc caacatcacc taagataaga atatataaca cagttatatc   7920
atatattgat agcaacaaga gaaacacaaa acaaactata catttgctta agagattgcc   7980
tgcagacgta cttaaaaaga caatcaagaa cactatagat attcacaacg aaataaatgg   8040
taataaccaa ggtgacataa ttgttaatga acaaaatgaa taactccaac attattattt   8100
tcccagaaaa atacccttgt agcatatcct ctttgctaat taagaatgaa aatgatgtta   8160
ttgtactaag tcatcaaaat gttcttgact acttacagtt tcaatatcca tgtaatatgt   8220
attctcaaaa tcatatgctt gatgatatct attggacatc acaggagcta attgaggatg   8280
tacttaagat tcttcatctt tctggcatat ccataagtaa gtatgtgata tatgttttag   8340
tgctatagta tataagtcac tcaactatta atcaacagcc acttcttcat agctagcaat   8400
atataaggac aaaatggata cactcattca tgagaactca actaatgttt acttaacaga   8460
tagttattta aaaggtgtca tctctttttc tgagtgcaat gccctgggaa gctacttgtt   8520
ggatggacct tatctaaaaa atgattatac caacatcata agtagacaga aaccattgat   8580
agaacatata aacttaaaaa aattgtctat catacagtct tttgtaacta agtataacaa   8640
aggagagctg ggtttagaag aacccactta ctttcaatct ttacttatga cttacaaaag   8700
tctgtctaca tcagaattaa tcacaactac aactctgttt aaaaagataa ttcgtagagc   8760
tatagaaata agtgatgtca aagtatatgc tatattgaac aaattgggtt taaaagaaaa   8820
gggaaaagtt gatagatgtg atgacactaa cacaacgcta tctaacatag taagagataa   8880
tatactctca gtcataagtg acaatactcc cagtactaaa aaaccaaata attcatcgtg   8940
taaaccagat cagccaatta aaacaacaat tttatgcaag cttttaagtt cgatgagtca   9000
tccccctaca tggttaatac attggtttaa tttatacaca aaattaaatg acatcttgac   9060
ccaatacaga acaaatgaag caagaaatca tggttacata cttatagata ctagaacctt   9120
gggtgaattc caatttatat taaatcaata tggttgcatt gtatatcata agaaattaaa   9180
gaaaattaca atcaccacat ataatcaatt tctaacatgg aaagacatta gcctcagtag   9240
attaaatgtt tgtatgatca cctggataag caattgttta aataccttga ataaaagcct   9300
tggattgaga tgtgagttta acaatgtcac tctatctcaa ttattccttc atggggattg   9360
tatattgaaa ttatttcata atgaaggtta ctatattata aaagaagttg aaggttttat   9420
aatgtcatta attttgaacc taacggaaga agatcaattc agaaaaagat tcttcaacag   9480
tatgctaaat aatattacag atgctgcagc aagagctcaa caagatttat tatcaagagc   9540
ccgccatact atattagaca aaacaatatc agataacata ttaaatggta aatggttaat   9600
tttattaggt aagtttctta aattgattaa attagctggt gctaataatc ttaataacct   9660
aagtgaactc tactttctct ttagaatatt tggacatccc atggtagatg aacggcaagc   9720
aatggatgct gtgagattaa actgtaatga aactaaattt tacttattga gtagccttag   9780
catgttaaga ggtgcattca tttatagaat tataaaggga tttgtaaaca catataatag   9840
gtggcctacc ttaaggaatg ctatagtttt acccttaaga tggataaatt actacaaact   9900
caatacttac ccatcattat tagaattaac agaagctgat ttgattatat tgtctggact   9960
gagattttat agagaattcc atctaccgaa aaaagtagat ttagaagtca taataaatga  10020
taaagcaata tcacctccca aaaaccttat ctggaccagt ttcccaaaaa actatatgcc  10080
```

```
atcacacata cagatttaca tagaacatga aagactaaag tttactgaga gtgatagatc  10140
tagaagggtt ctggaatatt atttaaggaa taatagattc agtgagagtg acctatataa  10200
ctgtatagta aaccaggaat atcttaataa tccaaaccat gtaatatcat taacaggaaa  10260
agaaagagaa cttagtgtag gtaggatgtt tgcaatgcag ccaggcatgt tcagacaggt  10320
tcaaatcatg gctgagaaat tgatagctga gaacatctta caatttttcc ctgagagttt  10380
aacacggtat ggagatcttg aattacagaa aatattagaa ttaaaagcag gcattagcaa  10440
caaagcaaat cgctgtaatg ataactataa caattatatc agtaaatgtt ctataatcac  10500
tgatcttagc aagttcaatc aggcattcag gtatgaaacg tcatgcattt gtagcgatgt  10560
tttagatgaa ttacatggtg tacaatctct cttttcttgg ttgcatttaa ctattccttt  10620
tgccactgtt atatgtactt atagacatgc tccaccttac ataagaaatc atataacaga  10680
tcttaataag gttgatgagc aaagtggact gtatagatat catatgggtg gtatagaagg  10740
ttggtgtcaa aaattgtgga ctattgaagc gatatcttta ttagatttaa tatctatcaa  10800
ggggaaattt tcaatcacag ctttaatcaa tggtgataat caatcaattg atataagtaa  10860
gcctatcaaa ttaaatgaag gacaaactca tgcacaggct gattatctat tagcacttaa  10920
aagccttaag ttgttgtata aagaatatgc tagtataggt cataaactta aaggtacgga  10980
gacatatata tcccgtgata tgcaatttat gagtaaaacc attcagcata atggtgtata  11040
ctatcctgca agcatcaaaa aagtgctacg agtaggtcca tggataaaca caatactgga  11100
tgattttaaa gtaagtatgg agtctatagg tagtttgact caagagttag aatatagagg  11160
agaaagttta ctatgcagtt tgatttttag gaatgtctgg ttgtataatc aaattgcttt  11220
gcaacttaag aatcatgcat tatgtcacaa caaactgtat ctagatatct tgaaagtgtt  11280
agcacactta aaaatgtttt ttaaccttga taatatagat actgccctaa cactatatat  11340
gaatttgcca atgttatttg gtggtggaga cccaaattta ttatatcgga gtttctatag  11400
aagaactccg gattttctta cagaagctat agcacattct gtctttgtgc ttagttatta  11460
tacaggacat gatcttcaag ataaattaca agatttacca gatgataaat taaataagtt  11520
tcttacatgt atcataactt ttgataagaa ccctaatgca gaatttgtaa cattgatgag  11580
agatccacaa gctttagggt ctgagagaca agctaaagtc actagtgaaa ttaatagatt  11640
agcagtgaca gaagtattaa gcaatgcacc aaataaaata tttgctaaaa gtgcacaaca  11700
ttacactact actgaagttg atttaaatga tgtaatgcaa aaaatagagc cgacttaccc  11760
gcatggatta agagtggtct atgaaagtct tcctttctac aaagcagaaa aaattgttaa  11820
tttaatatca ggcactaaat ctatcaccaa tatacttgaa aaaacatctg ctattgatta  11880
tacagacatt gagagagcta tagatatgat gagaaagaat ataactttgc taattagaat  11940
tcttccatta gattacaata aagccaagtt gggattgtta agtctcaaca atcttagtat  12000
cactgatata agtaaatatg taagagaaag atcttggtca ctgtctaaca ttgtaggtat  12060
tacatctcct agcatattat atacaatgga tattaaatac accactagca ctataactag  12120
tggtataata attgaaaaat acaattccaa ttttttgact cgtggtgaga ggggtcccac  12180
taaaccatgg gtaggatcat caacccaaga aaagaaaaca atgcctgtat acaataggca  12240
ggttttaact aagaaacaaa aggatcaaat tgatttgttg gcaaaactag attgggttta  12300
tgcctctata gataacaaag atgagtttat ggaagtatta tgtttgggaa cacttggact  12360
atcctatgaa aaagccaaga aattgttccc tcaataccttg agtgtaaact acctgcatcg  12420
tcttacagtt agtagtagac catgtgagtt tccagcctca ataccagctt acagaacaac  12480
```

```
taattaccac tttgacacaa gtccaattaa tcgaatacta actgaaaaat atggtgatga  12540
agacattgat atagtgtttc agaattgtat cagttttggt cttagcttaa tgtcagttgt  12600
agaacaattt acaaatgtat gcccaaatag aattattcta ataccaaaac ttaatgaaat  12660
tcatttgatg aagccaccca tatttacagg tgatgttgac atttgtaagc ttaatcaggt  12720
gatacagaaa cagcatatgt ttttacctga taaaatcagt ttgtctcaat atgttgaatt  12780
gttccttagc aataaaacac ttaagaatag tccacatata agctctaatt tagtgttagt  12840
gcacaaaatg tctgattact tttgcataa gtatgtttta agcacaaact tagcaggaca  12900
ttggataatg atcatacagc ttatgaaaga ttctaaaggg atttttgaga aggattgggg  12960
tgaaggatat ataactgatc atatgttttt agatttaaat gtcttttttg atgcatataa  13020
aacatatttg ttatgttttc ataaaggtta tggaaaagct aaattagaat gtgatatgaa  13080
tacatcagat ctttttgta cattagagtt aatagatatc agctattgga aatccatgtc  13140
caaggtgttc ttagaacaaa aagtagtgaa gcacataatt aatcaagatt ctagtctaca  13200
tagagtaaga gggtgccata gttttaagtt atggttcctt aagcgtctta atacatctaa  13260
gttcattgtt tgtccttggg tagtcaatat agattatcat ccaactcata tgaaagccat  13320
attgacttac atggagttga ctactatggg gttagtccat gtagacaaac tatacacaga  13380
ccaaaaacat aaactaaatg atggatttta cacatcaaat ctattttata tcaattataa  13440
tttttcagat aatacacact tgttaactaa acagataaga gtagcaaatt cagagttaat  13500
agataactat aatacattgt atcatccatc tcctgaatct ttagaaagta ttttaaaaag  13560
gtctaatcaa agtaataatg taattgaatt gaaagactat cccatagata aattccaatc  13620
tccaaaggga cggggggtct cagacataac atgcataagc tctaaccaaa aaataaaaca  13680
aggttataac aatcaagatc tgtacaatct atttccagca gtaataatag acaagattgt  13740
agatcattca ggtaacattg caaacatcaa ccaaatgtat acaattactc caaatcaact  13800
tacattaata agtaatggta cttcattata ctgtatgctt ccgtggcatc atataaatag  13860
gtttaatttt gtgtttagct ccactggttg caaaattagt acaaaactta tacttaagga  13920
tcttaaaata aaggatcctc attgtatagc ctttataggg gaaggggcag gaaatttgtt  13980
gttacgcaca gtagtggaat tacatccaga cataaaatat atttatagaa gtctaaaaga  14040
ttgtaatgat catagtttac caattgagtt tctaagatta tacaatggcc atataagtat  14100
agattatgga gaaaatctaa ctataccagc cactgatgca accaatgcta tacattggtc  14160
ttacttacat ataagatatg cagaacccat aaatcttttt gtatgtgatg ctgagttacc  14220
tgatttaact aactggagta gaattgtttc agaatggtat aagcatgtta gatgttgcaa  14280
gtattgctct acaattgacc gaagtaaatt aattgtaaaa tatcatgcac aagatatcac  14340
tgatttcaaa ttaaataaca tatcaatagt caaaacatat gtgtgcttag gtagtaagct  14400
gaaaggttct gaggtttatt tagtccttac agttggtcca tctaatatat ttccatcttt  14460
caatgtagtg cagaatgcta agttgatact ttcaaggaca caaaattttc ccatgcctaa  14520
gaagattgac aaggattcag tagatgcaaa tatcaaaagt ttgataccgt ttctttgtta  14580
tcctataact aagaaaggga taaaggcagc attatctaag ttaaaagatg tggtagatgg  14640
aaacatttta tcatattcta tagcagggcg aaatgaagtt tatagtaaca agcttataaa  14700
ctataaattg ttaaacatcc taaaatggtt agatcatata ttaaattttc gatctctaga  14760
gttcagctat aatcacttat atatgattga atcaacatat cctttcttaa gtgagttact  14820
```

-continued

```
aaacagtttg actactaatg aacttaaaaa attaattaag gtaacaggga gtgtattata  14880

tagtcttcag catgaattgt aagactcata acactttggt gtgattcatt ttacaaccat  14940

gattatatgt aatgtaatat caatatagtt atttaaaaac tcacattatc tatatagttg  15000

ttaatcttaa attcccacat atctgtgttc caactcaaat tccactggtc aagatctaaa  15060

ccagaaaatc aaaaatttaa tggtacgaga atatgtcctt tatgttgcaa gaggatagtt  15120

tttgatactt tttttctcgt                                              15140
```